US012793850B2

(12) United States Patent
Sun et al.

(10) Patent No.: US 12,793,850 B2
(45) Date of Patent: Nov. 10, 2026

(54) METHOD AND SYSTEM FOR DIAGNOSTIC ANALYZING

(71) Applicant: Roche Diagnostics Operations, Inc., Indianapolis, IN (US)

(72) Inventors: Wen Sun, Shanghai (CN); Renzhong Sun, Shanghai (CN); Chenxi Zhang, Beijing (CN); Qi Zhou, Shanghai (CN)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 193 days.

(21) Appl. No.: 18/296,040

(22) Filed: Apr. 5, 2023

(65) Prior Publication Data

US 2023/0238139 A1 Jul. 27, 2023

Related U.S. Application Data

(63) Continuation of application No. PCT/CN2020/120239, filed on Oct. 10, 2020.

(51) Int. Cl.
*G16H 50/20* (2018.01)

(52) U.S. Cl.
CPC .................................. *G16H 50/20* (2018.01)

(58) Field of Classification Search
USPC .......................................................... 705/2–3
See application file for complete search history.

(56) References Cited

U.S. PATENT DOCUMENTS 10,726,356 B1 7/2020 Zarandioon et al.
11,972,336 B2 * 4/2024 Vaughan ............... A61B 5/1118
2005/0071143 A1 * 3/2005 Tran ....................... G16B 25/30 703/11

(Continued)

FOREIGN PATENT DOCUMENTS

CN 1760881 A 4/2006
CN 103885898 A 6/2014

(Continued)

OTHER PUBLICATIONS

Valencia-Zapata, G. (2019). Probabilistic diagnostic model for handling . . . machine learning (Order No. 30502991). Available from ProQuest Dissertations and Theses Professional. (2827702435). Retrieved from https://dialog.proquest.com/professional/docview/2827702435?accountid=131 (Year: 2019).*

(Continued)

*Primary Examiner* — Bennett Stephen Erickson
(74) *Attorney, Agent, or Firm* — Lee & Hayes, P.C.

(57) ABSTRACT

Embodiments of the present disclosure relate to method and system for diagnostic analyzing. Some embodiments of the present disclosure provide a diagnostic analyzing system. The diagnostic analyzing system comprises one or more analyzer instruments and a monitoring system, e.g. a quality control monitoring system. The one or more analyzer instruments designed for providing an analytical testing result, which is to be validated by the monitoring system using a validation algorithm. Moreover, the monitoring system may re-train the validation algorithm when a difference level between a live data set and a first training data set is greater than a threshold. Through the solution, it is possible to improve the accuracy of the validation algorithm.

22 Claims, 7 Drawing Sheets

(56) References Cited

U.S. PATENT DOCUMENTS

| | | | |
|---|---|---|---|
| 2008/0222058 A1 | 9/2008 | Doctor et al. | |
| 2009/0093995 A1 | 4/2009 | Woosley et al. | |
| 2010/0304989 A1* | 12/2010 | Von Hoff | B01L 7/52 506/9 |
| 2013/0089248 A1 | 4/2013 | Remiszewski et al. | |
| 2013/0198119 A1 | 8/2013 | Eberhardt, III et al. | |
| 2016/0358088 A1 | 12/2016 | Lemmer et al. | |
| 2017/0185913 A1 | 6/2017 | Codella et al. | |
| 2019/0156241 A1* | 5/2019 | Hughes | G06F 16/25 |
| 2019/0221313 A1 | 7/2019 | Rim et al. | |
| 2020/0019884 A1* | 1/2020 | McCourt, Jr. | G06N 20/00 |
| 2020/0168320 A1 | 5/2020 | Hu | |
| 2020/0303074 A1* | 9/2020 | Mueller-Wolf | A61B 5/021 |
| 2020/0311595 A1 | 10/2020 | Chen et al. | |
| 2021/0201190 A1* | 7/2021 | Edgar | G06N 20/00 |
| 2021/0327056 A1* | 10/2021 | Needham | G06T 7/30 |
| 2022/0054008 A1* | 2/2022 | Venkatraman | G16H 50/70 |

FOREIGN PATENT DOCUMENTS

| | | | |
|---|---|---|---|
| CN | 105786699 | A | 7/2016 |
| CN | 109934341 | A | 6/2019 |
| CN | 110472743 | A | 11/2019 |
| CN | 110739076 | A | 1/2020 |
| CN | 2020013529 | A | 1/2020 |
| CN | 111512316 | A | 8/2020 |
| CN | 111652327 | A | 9/2020 |
| CN | 111671408 | A | 9/2020 |
| JP | 2019091324 | A | 6/2019 |
| JP | 2019109553 | A | 7/2019 |
| KR | 10-2018-0028888 | A | 3/2018 |
| WO | 2004/063831 | A2 | 7/2004 |
| WO | 2019/153039 | A1 | 8/2019 |
| WO | 2020/036007 | A1 | 2/2020 |

OTHER PUBLICATIONS

H. Homayouni, S. Ghosh and I. Ray, "ADQuaTe: An Automated Data Quality Test Approach for Constraint Discovery and Fault Detection," 2019 IEEE 20th International Conference on Information Reuse and Integration for Data Science (IRI), Los Angeles, CA , USA, 2019, pp. 61-68, doi: 10.1109/IRI.2019.00023. (Year: 2019).*

Chinese Search Report issued Jun. 12, 2023, in Application No. 2020800975965, 2 pp.

International Search Report issued Jul. 14, 2021, in Application No. PCT/CN2020/120239, 4 pp.

Search Report issued with Notice of Grant Sep. 21, 2023, in Chinese Application No. 2020800975965, 3 pp.

Ahmed, Chowdhury Farhan et al., Reframing Continuous Input Attributes, IEEE 26th International Conference on Tools with Artificial Intelligence, pp. 31-38, 2014.

Chen, Zhuyun et al., Intelligent Fault Diagnosis for Rotary Machinery Using Transferable Convolutional Neural Network, IEEE Transactions on Industrial Informatics, vol. 16, No. 1, pp. 339-349, 2020.

Shen, Weijun et al., Multiple-Boundary Clustering and Prioritization to Promote Neural Network Retraining, 35th IEEE/ACM International Conference on Automated Software Engineering (ASE), pp. 410-422, 2020.

Supplemental European Search Report issued Jun. 13, 2024, in Application No. 20956559.7, 3 pp.

Translated Japanese Office Action for related Japanese Patent Application No. 2023-521670, dated Dec. 3, 2024, 6 pages.

Kaehler, et al., "Detailed Explanation OpenCV3," Image Processing and Recognition using Computer Vision Library, 1st Ed, Japan, O'Reilly Japan, Inc., May 28, 2018, 4 pages.

* cited by examiner

METHOD AND SYSTEM FOR DIAGNOSTIC ANALYZING

CROSS-REFERENCE TO RELATED APPLICATIONS

This application is a continuation of International Patent Application No. PCT/CN2020/120239 filed Oct. 10, 2020, the disclosure of which is hereby incorporated by reference in its entirety.

FIELD

The invention relates to analytical testing and monitoring, e.g. quality control monitoring, thereof, for example in the field of health related diagnostics.

BACKGROUND

Diagnostic analytical testing can provide physicians with pivotal information and thus can be of great importance for health related decisions, population health management, etc.

Analytical testing can be subject to errors that can compromise the analytical testing results. The errors can e.g. be due to mishandling, misconfiguration, and/or tear of an analyzer. There is a need to detect such errors; a detection can e.g. be the first step towards removing the cause of an error.

SUMMARY

It is the purpose of this invention to provide systems, methods, and mediums that expand the current state of the art.

For this purpose, systems, methods, and mediums according to the independent claims are proposed and specific embodiments of the invention are set out in the dependent claims.

A diagnostic analyzing system is proposed, the diagnostic analyzing system comprising:

- one or more analyzer instruments (10) designed for providing an analytical testing result;
- a monitoring system (20) designed for processing an analytical testing data,
  - the analytical testing data comprising an analytical testing result provided by the one or more analyzer instruments (10) and metadata associated with the analytical testing result,
- the monitoring system (20) being designed for validating an analytical testing result using a validation algorithm,
  - the validation algorithm being trained using a first training data set comprising a plurality of training analytical testing data, each training analytical testing data comprising a training analytical testing result and training metadata, and
- the monitoring system (20) being designed for
  - evaluating a difference level between a live data set of analytical testing data and the first training data set,
    - the difference level being determined based on a comparison of distribution characteristics of the live data set and the first training data set, and
  - re-training the validation algorithm using a second training data set if the difference level between the live data set and the first training data set is greater than a first threshold, and
  - using the re-trained validation algorithm for validation of an analytical testing result.

According to some embodiments, a difference level between the live data set and the second training data set is lower than a second threshold.

According to some embodiments, wherein the second training data set comprises the live data set.

According to some embodiments, the monitoring system (20) is designed for: performing an analysis of the analytical testing results and the results of the validation algorithm.

According to some embodiments, the monitoring system (20) is designed for informing a user of the monitoring system (20) of a possible error associated with the analyzing testing process based on the analysis.

According to some embodiments, at least one of the one or more analyzer instruments (10) is a biological sample analyzer designed for processing biological samples and providing an analytical testing result associated with the biological sample.

According to some embodiments, a distribution characteristic of a data set is determined using a value of the analytical testing result included in the data set.

According to some embodiments, a distribution characteristic of a data set is determined using metadata associated with the analytical testing result included in the data set.

According to some embodiments, the metadata at least comprises at least one of: an age of a patient associated with the analytical testing result; a gender of the patient; a type of sourcing of the patient; a ward of the patient; and a health diagnosis of the patient.

According to some embodiments, the monitoring system (20) is designed for: determining a first characteristic value based on metadata associated with the live data set; determining a second characteristic value based on metadata associated with the first training data set; and evaluating the difference level using the first characteristic value and the second characteristic value.

According to some embodiments, the monitoring system (20) is designed for: determining a first association between a first feature of the live data set and a first set of ground-truth labels associated with the live data set, the first set of ground-truth labels being indicative of a validity value of each of the plurality of analytical testing data included in the live data set; determining a second association between a second feature of the first training data set and a second set of ground-truth labels associated with the first training data set, the second set of ground-truth labels being indicative of a validity value of each of the plurality of training analytical testing data included in the first training data set; and evaluating the difference level using the first association and the second association.

According to some embodiments, the monitoring system (20) is designed for: determining a first percentage of analytical testing results of the live data set that are labeled as invalid; determining a second percentage of analytical testing results of the first training data set that are labeled as invalid; evaluating the difference level using the first percentage and the second percentage.

According to some embodiments, the monitoring system (20) is designed for: obtaining a first performance associated with the original validation algorithm; determining a second performance associated with the re-trained validation algorithm by processing a testing data set with the re-trained validation algorithm, wherein the testing data set comprises a plurality of analytical testing data; and if the second performance is better than the first performance, using the re-trained validation algorithm for validation of an analytical testing result.

According to some embodiments, the training data set are processed by the re-trained validation algorithm according to an order, and wherein the monitoring system (20) is designed for: determining a first number, the first number being the number of analytical testing results that have been processed by the re-trained validation algorithm before a faulty invalidation is made by the re-trained validation algorithm according to the order; determining a second number, the second number being the number of analytical testing results before an analytical testing result that is labeled as invalid is processed according to the order; and determining the second performance using the first number of analytical testing data and the second number of analytical testing data.

According to some embodiments, the monitoring system (20) is designed for: determining a number of faulty validation predictions and/or faulty invalidation predictions by the re-trained validation algorithm based on the testing data set; and determining the second performance using the number of faulty validation predictions and/or faulty invalidation predictions by the re-trained validation algorithm.

A computer-implemented method for quality control monitoring of diagnostic analytical testing is proposed, the method comprising:

receiving (202) a live data set comprising a plurality of analytical testing data, each analytical testing data comprising an analytical testing result and metadata associated with the analytical testing result;

validating (204) an analytical testing result of the live data set using a validation algorithm;

the validation algorithm being trained using a first training data set comprising a plurality of training analytical testing data, each training analytical testing data comprising a training analytical testing result and training metadata; and evaluating (206) a difference level between the live data set and the first training data set, the difference level being determined based on comparison of distribution characteristics of the live data set and first training data set; and re-training (210) the validation algorithm using a second training set if the difference level between the live data set and the first training data set is greater than a first threshold.

A method for monitoring of diagnostic analytical testing is proposed, the method comprising:

determining a plurality of analytical testing results;

providing a live data set comprising a plurality of analytical testing data, each analytical testing data comprising an analytical testing result of the plurality of analytical testing results and metadata associated with the analytical testing result; and performing the steps of the computer-implemented method for quality control monitoring of diagnostic analytical testing.

A diagnostic analyzing system (1) is proposed, the diagnostic analyzing system (1) comprising:

one or more analyzer instruments (10) designed for determining analytical testing results;

a monitoring system (20) being configured for performing the computer-implemented method for quality control monitoring of diagnostic analytical testing.

A monitoring system (20) for diagnostic analytical testing is proposed, wherein the monitoring system (20) is designed for:

processing an analytical testing data, the analytical testing data comprising an analytical testing result provided by one or more analyzer instruments (10) and metadata associated with the analytical testing result, validating an analytical testing result using a validation algorithm, the validation algorithm being trained using a first training data set comprising a plurality of training analytical testing data, each training analytical testing data comprising a training analytical testing result and training metadata, and evaluating a difference level between a live data set of analytical testing data and the first training data set, the difference level being determined based on a comparison of distribution characteristics of the live data set and the first training data set, and re-training the validation algorithm using a second training data set if the difference level between the live data set and the first training data set is greater than a first threshold, and using the re-trained validation algorithm for validation of an analytical testing result.

A computer-implemented method for monitoring of diagnostic related analytical testing is proposed, the method comprising:

processing an analytical testing data, the analytical testing data comprising an analytical testing result provided by one or more analyzer instruments (10) and metadata associated with the analytical testing result, validating an analytical testing result using a validation algorithm, the validation algorithm being trained using a first training data set comprising a plurality of training analytical testing data, each training analytical testing data comprising a training analytical testing result and training metadata, and evaluating a difference level between a plurality of analytical testing data being processed and the first training data set, the difference level being determined based on a comparison of distribution characteristics of the plurality of analytical testing data being processed and the first training data set.

A monitoring system (20) for diagnostic analytical testing is proposed, the system comprising: a processing unit (701); and a memory (702, 703) coupled to the processing unit and having instructions stored thereon that, when executed by the processing unit, cause the electronic device to perform the computer-implemented method for quality control monitoring of diagnostic analytical testing.

A computer-readable medium is proposed, the computer-readable medium comprising instructions that when executed cause performing the computer-implemented method for quality control monitoring of diagnostic analytical testing.

It is to be understood that the summary section is not intended to identify key or essential features of embodiments of the present disclosure, nor is it intended to be used to limit the scope of the present disclosure. Other features of the present disclosure will become easily comprehensible through the following description.

BRIEF DESCRIPTION OF THE DRAWINGS

Through the following detailed description with reference to the accompanying drawings, the above and other objectives, features, and advantages of example embodiments of the present disclosure will become more apparent. In the example embodiments of the present disclosure, the same reference numerals usually refer to the same components.

DETAILED DESCRIPTION

Principle of the present disclosure will now be described with reference to some embodiments. It is to be understood that these embodiments are described only for the purpose of illustration and help those skilled in the art to understand and implement the present disclosure, without suggesting any limitation as to the scope of the disclosure. The disclosure described herein can be implemented in various manners other than the ones described below.

In the following description and claims, unless defined otherwise, all technical and scientific terms used herein have the same meaning as commonly understood by one of ordinary skills in the art to which this disclosure belongs.

References in the present disclosure to "one embodiment," "an embodiment," "an example embodiment," and the like indicate that the embodiment described may include a particular feature, structure, or characteristic, but it is not necessary that every embodiment includes the particular feature, structure, or characteristic. Moreover, such phrases are not necessarily referring to the same embodiment. Further, when a particular feature, structure, or characteristic is described in connection with an example embodiment, it is submitted that it is within the knowledge of one skilled in the art to affect such feature, structure, or characteristic in connection with other embodiments whether or not explicitly described.

It shall be understood that although the terms "first" and "second" etc. may be used herein to describe various elements, these elements should not be limited by these terms. These terms are only used to distinguish one element from another. For example, a first element could be termed a second element, and similarly, a second element could be termed a first element, without departing from the scope of example embodiments. As used herein, the term "and/or" includes any and all combinations of one or more of the listed terms.

The terminology used herein is for the purpose of describing particular embodiments only and is not intended to be limiting of example embodiments. As used herein, the singular forms "a", "an" and "the" are intended to include the plural forms as well, unless the context clearly indicates otherwise. It will be further understood that the terms "comprises", "comprising", "has", "having", "includes" and/or "including", when used herein, specify the presence of stated features, elements, and/or components etc., but do not preclude the presence or addition of one or more other features, elements, components and/or combinations thereof.

Figure 1:
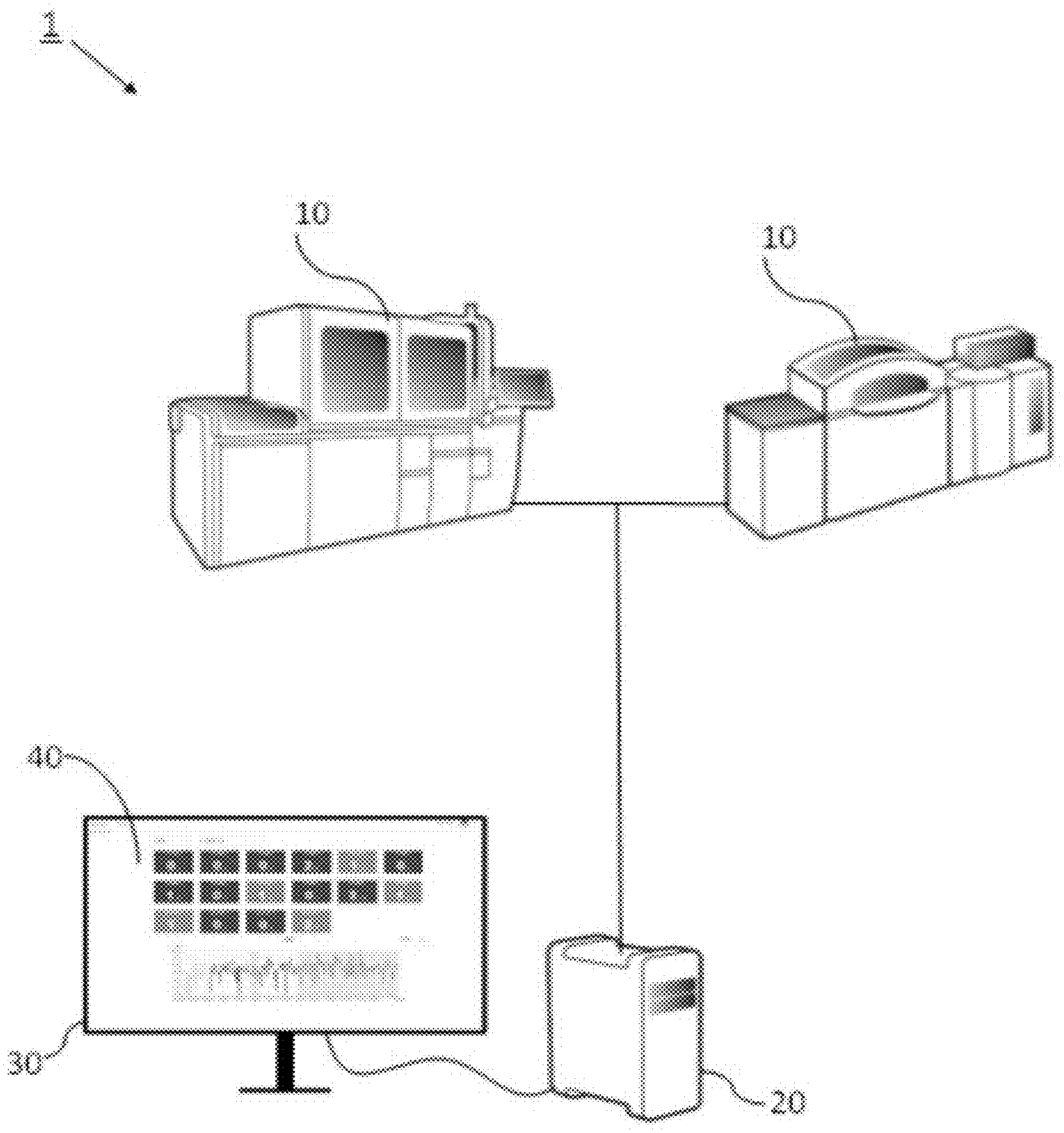
FIG. 1 illustrates a schematic diagram of an exemplary diagnostic analyzing system according to an implementation of the subject matter described herein.

As discussed above, validation procedures are important to ensure validity of analytical testing results that are generated in various diagnostic tests. FIG. 1 illustrates a schematic diagram of an exemplary diagnostic analyzing system (1) according to an implementation of the subject matter described herein.

As shown in FIG. 1, the diagnostic analyzing system (1) may comprise one or more analyzer instruments (10) for determining analytical testing results and a monitoring system (20). An analyzer instrument (10), or in short "analyzer", is an apparatus and/or software designed to perform an analytical function and obtain an analytical testing result. A diagnostic analytical testing result can be indicative of a health related status.

According to some embodiments, at least one of the one or more analyzers (10) is designed to carry out analysis of biological samples, e.g. samples for in vitro diagnostics ("IVD") that were derived from a biological source. According to some specific embodiments, the at least one analyzer (10) is designed to determine via various chemical, biological, physical, optical, and/or other technical procedures a parameter value of the biological sample or a component thereof and use the parameter value for obtaining an analytical testing result. Examples of biological sample analyzers comprise e.g. laboratory systems such as the Cobas® 8800 System and Point-of-Care systems such as the Accu-Chek® Inform II.

According to some embodiments, at least one of the one or more analyzers (10) is designed to collect digital data and use the digital data for obtaining a diagnostic analytical testing result. In an example, the at least one analyzers (10) is designed to collect data indicative of a movement of a patients finger and/or eyes, e.g. in reaction to a stimulus, and to provide a quantitative and/or qualitative result for calculating an analytical testing result. An example of a digital analyzer is the App Floodlight.

For ensuring the validity of the analytical testing result provided by the analyzer (10), the monitoring system (20) may retrieve the analytical testing data and validate the analytical testing result comprised therein. An accumulation of invalidations of analytical testing results that have something in common, e.g. that they are provided by a certain analyzer or by a certain group of analyzers that share a common resource (e.g. a reagent lot or a preprocessing instrument), can be an indication of a systematic error in the analytical testing process.

According to some embodiments, the monitoring system (20) is designed as a quality control monitoring system. The quality control monitoring system can e.g. be designed for performing an analysis of the analytical testing results and the results of the validation algorithm. According to some specific embodiments, the analysis is performed on testing results which are deemed as invalid by the validation algorithm. The analysis may e.g. indicate that a certain plurality of analytical testing results are deemed too high (or too low), which can be indicative of a systematic error in the analytical testing process. A result of the analysis could e.g. be that analytical testing results that are deemed invalid have something in common, which can lead to a source of errors in the analytical testing process. The analysis can comprise a statistical analysis.

According to some embodiments, the monitoring system (20) may be deployed with a validation algorithm for validating the retrieved analytical testing results based on analytical testing data comprising the analytical testing results and metadata associated to each analytical testing result. The validation algorithm may for example be implemented through machine learning techniques. The machine learning techniques may also be referred to as artificial intelligence (AI) techniques. Examples of the validation algorithm comprise, but are not limited to, various types of deep neural networks (DNN), convolutional neural networks (CNN), support vector machines (SVM), decision trees, random forest models, and so on. The validation algorithm can e.g. classify an analytical testing result as "deemed invalid" or "deemed valid". According to some embodiments, the validation algorithm can provide a quantification of the degree to which an analytical testing result is deemed invalid resp. deemed valid. Such a degree can be used in an analysis of the results of the validation algorithm.

According to some embodiments, the validation algorithm is a quality control algorithm and/or is comprised in a quality control algorithm. The quality control algorithm can e.g. be designed for detecting errors, e.g. systematical errors, based on the validation presumptions for the analytical testing results made by the validation algorithm. According to some specific embodiments, a quality control algorithm comprises the validation algorithm and an analysis algorithm designed for analysis of the analytical testing results and the respective validity presumptions made by the validation algorithm. The analysis algorithm can comprise a statistical analysis algorithm that implements statistical methods. The quality control algorithm can further be designed for indicating possible errors, e.g. a systematic error, in the analytical testing process based on the results if the analysis algorithm. According to some specific embodiments, the quality control algorithm can further be designed for indicating possible sources of errors in the analytical testing process.

According to some embodiments, the monitoring system (20) is comprised in and/or or connected to a middleware such as Cobas® infinity laboratory solution or Cobas® infinity POC solution. According to some specific embodiments, the analytical testing data or at least parts thereof, e.g. the analytical testing results, are provided to the monitoring system (20) by the middleware.

According to some embodiments, the monitoring system (20) is comprised in and/or or connected to a laboratory information system ("LIS") or hospital information system ("HIS"). According to some specific embodiments, the analytical testing data or at least parts thereof, e.g. at least part of the metadata, are provided to the monitoring system (20) by an LIS or HIS.

According to some embodiments, the monitoring system (20) comprises software components. At least some of the software components can be designed for running as a cloud application, e.g. on one or more server. According to some specific embodiments, the monitoring system (20) comprises software components and hardware components.

As shown in FIG. 1, the monitoring system (20) may be further coupled to a display (30) and provide via the display (30) information about validity of the analytical testing results determined by the monitoring system (20). For example, the display (30) may show statistics of validity statuses of the analytical testing results determined by the monitoring system (20), and may use a different color for indicating an analytical testing result is deemed invalid by the monitoring system (20).

According to some embodiments, as shown in FIG. 1, the monitoring system (20) may present a graphical user interface (GUI) (40) on the display (30), which may show various information related to the monitoring of the analytical testing results. For example, the GUI (40) may show a doctor or a nurse how many analytical testing results have been generated by the analyzer (10) each day and how many of them are deemed invalid by the monitoring system (20).

According to some embodiments, the GUI (40) may also allow a doctor or a nurse to input his/her feedback regarding the validity prediction of an analytical testing result. For example, a doctor may provide a feedback that an analytical testing result is incorrectly deemed as invalid by the validation algorithm, or a feedback that an analytical testing result is incorrectly deems as valid by the validation algorithm.

In current validation procedures, the validation algorithm is typically trained using a specific training data set. Typically, in a case that a machine learning validation algorithm is used, the validation algorithm may achieve a good performance when an overall characteristic of input analytical testing results is close to the training analytical testing results included the training data set.

However, if an overall characteristic of the input analytical testing results is significantly different from the training analytical testing results, more faulty validation predictions or faulty invalidation predictions may then be generated by the validation algorithm. For example, if the validation algorithm is trained using analytical testing results generated in summer, the validation algorithm may be error prone when processing analytical testing results generated in a different season, e.g., winter. Therefore, it is desired to obtain a solution for improving the accuracy of the invalidation procedure.

According to example embodiments of the present disclosure, there is proposed a solution for automated validation of medical data. In this solution, a live data set comprising a plurality of analytical testing data is provided, wherein each analytical testing data comprises an analytical testing result and metadata associated with the analytical testing result. The analytical testing results of the live data set is validated using a validation algorithm, wherein the validation algorithm has been trained using a first training data set comprising a plurality of training analytical testing data, wherein each training analytical testing data comprises a training analytical testing result and training metadata. Before, during, and/or after the processing of the live data, a difference level between the live data set and the first training data set is evaluated, wherein the difference level is determined based on comparison of distribution characteristics of the live data set and first training data set. If the difference level between the live data set and the first training data set is greater than a threshold, the validation algorithm is then re-trained using a second training set. Then, the re-trained validation algorithm is used for future validation of an analytical testing result. In this manner, the validation algorithm may be re-trained, e.g. automatically, which can thus significantly improve accuracy and quality of validation of analytical testing data.

Figure 2:
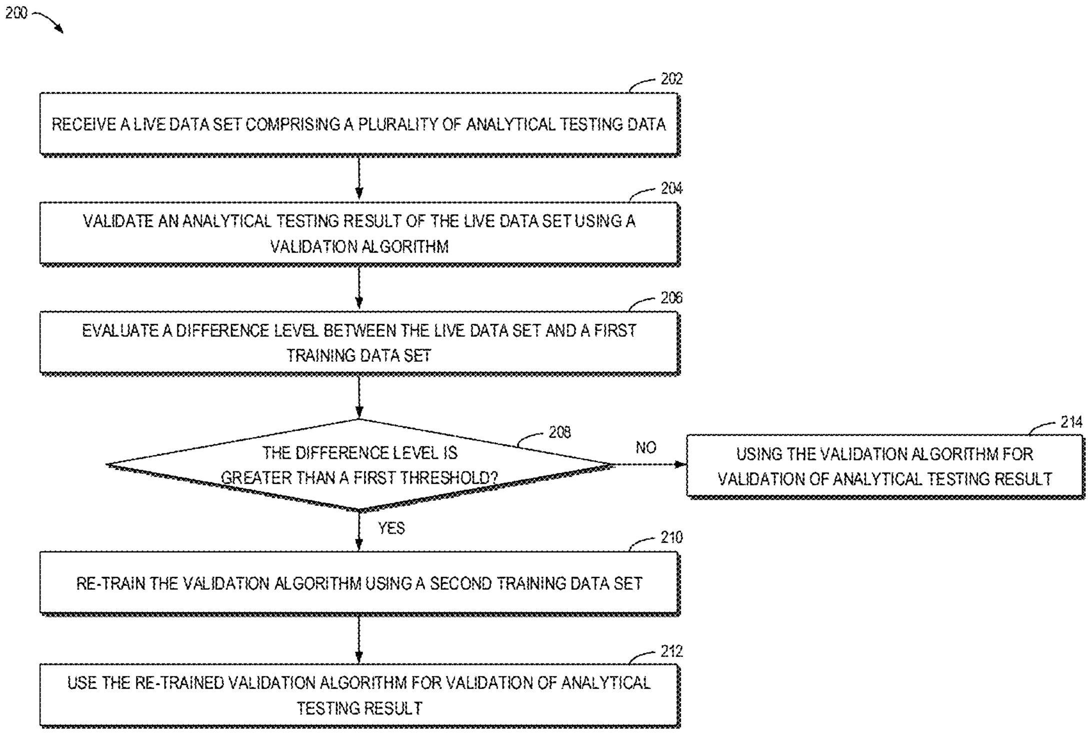
FIG. 2 illustrates a flowchart of a process for monitoring of diagnostic analytical testing according to an implementation of the subject matter described herein.

In the following, example embodiments of the present disclosure are described with reference to the drawings. Reference is first made to FIG. 2, which illustrates a flowchart of a process (200) for quality control monitoring of diagnostic analytical testing according to an implementation of the subject matter described herein. The monitoring herein may comprise quality control monitoring for detecting an error in the analytical testing process.

As shown in FIG. 2, at block 202, the monitoring system (20) receives (202) a live data set comprising a plurality of analytical testing data, wherein each analytical testing data comprises an analytical testing result and metadata associated with the analytical testing result. Examples of a live data set may comprise the analytical testing data which are currently processed by a validation algorithm. For example, a live data set may comprise a plurality of testing data which have been processed in a current day.

As discussed above, the monitoring system may retrieve the plurality of analytical testing results provided by the analyzers (10). According to some embodiments, each analytical testing data may comprise one or more testing results associated with a single patient. For example, in an example of blood sample testing, two or more analytical testing results associated with blood analysis may be provided by the analyzers (10), e.g., an amount of white blood cell (WBC) and an amount of red blood cell (RBC).

According to some embodiments, the monitoring system (20) may also receive the metadata associated with the analytical testing result. The metadata for example may indicate a property of a patient associated with the analytical testing result. According to some embodiments, the metadata may comprise a plurality of aspects, each of which indicates a corresponding property of a patient.

According to some embodiments, the metadata associated with an analytical testing result may comprise an age of a patient associated with the analytical testing result. In some cases, the age may for example be expressed using a numerical value, e.g., thirty, which indicates that the patient is thirty years old. Alternatively, an age of a patient may also be expressed using a corresponding label, e.g., a string, for indicating a range of the age, e.g., a baby patient, a teenager patient, a middle-aged patient, an old patient and the like.

According to some embodiments, the metadata associated with an analytical testing result may also comprise a gender of a patient associated with the analytical testing result. For example, the gender information included in the metadata may show whether the patient is female or male. Similarly, the gender information could be expressed either by a numerical value. For example, a numerical value "one" may indicate that the patient is male, and a numerical value "zero" may indicate that the patient is female. Alternatively, the gender information could also be expressed using a string, e.g., "male" or "female".

According to some embodiments, the metadata associated with an analytical testing result may also comprise a type of a source of a patient associated with the analytical testing result. In some embodiments, the type of a source of a patient may indicate whether the patient is in-patient or out-patient. Alternatively, the type of a source of a patient may indicate at which entity a sample of the patient is taken, e.g., a hospital or a laboratory.

According to some embodiments, the metadata associated with an analytical testing result may also comprise a ward of a patient associated with the analytical testing result. For example, the ward information included in the metadata may indicate which ward the patient is from, e.g., a cardiology ward, a surgical ward and the like. Alternatively, the ward information may also indicate whether the patient's ward is a high-risk ward. A high-risk ward herein may indicate that a probability that analytical testing results of patients in this ward are abnormal (i.e., a value is beyond a normal range) would be greater than patients in another ward. For example, a hepatology ward is a high-risk ward in the regard of analytical testing of ALT (Alanine aminotransferase).

According to some embodiments, the metadata associated with an analytical testing result may also comprise a health diagnosis of a patient associated with the analytical testing result. For example, the health diagnosis may be provided by a doctor before reviewing the analytical testing result, e.g., diabetes, hypertension and the like. In another example, the heath diagnosis may be a historical health diagnosis of the patient before the diagnostic analytical test.

In some instances, the heath diagnosis included in the metadata may also be expressed using a binary value for indicating whether the health diagnosis associated with the patient belongs to a particular set of diseases which may lead to a higher probability of abnormal analytical testing results. For example, in a diagnosis analytical testing of ALT, hepatitis would be deemed as a disease which may lead to a higher probability of abnormal analytical testing results.

According to some embodiments, the metadata associated with an analytical testing result may also comprise two of more of the various types of metadata as discussed above. For example, the metadata may comprise all of the information: an age of the patient, a gender of the patient, a type of the source of the patient, a ward associated with the patient, and a health diagnosis associated with the patient.

According to some embodiments, an HIS or an LIS may collect such metadata and then provide the metadata to the monitoring system (20) as part of the live data set. As will be discussed later, the metadata along with the analytical testing result may be applied to the validation algorithm for validating the analytical testing result.

At block 204, the monitoring system (20) validates (204) an analytical testing result of the live data set using a validation algorithm, wherein the validation algorithm is trained using a first training data set comprising a plurality of training analytical testing data, and wherein each training analytical testing data comprise a training analytical testing result and training metadata.

As discussed above, the validation algorithm may be implemented through machine learning techniques. According to some embodiments, during the training of the validation algorithm, a feature vector to be applied to the validation algorithm may be determined based on the plurality of training analytical testing results and the training metadata. It should be understood that, the training metadata may indicate the same properties as the metadata included in the live data set as discussed above.

For example, a feature vector with 6 dimensions may be determined based on the first training data set and then applied to the validation algorithm for training. For example, the 6 dimensions of features included in the feature vector may comprise: analytical testing result, age, gender, type of source, ward and health diagnosis.

According to some embodiments, a numerical value may be used in the feature vector for indicating corresponding information. For example, en exemplary feature vector may be {500, 30, 1, 1, 1, 0}, wherein a value "500" of the "analytical testing result" feature may indicate the analytical testing result is "500", a value "30" of the "age" feature may indicate the patient is 30 years old, a value "1" of the "gender" feature may indicate that the patient is male, a value "1" of the "ward" feature may indicate that the ward of the patient belongs to a high-risk ward as discussed above, and a value "0" of the "health diagnose" feature may indicate that there is no health diagnose associated with the patient or the health diagnose associated with the patient doesn't belong to a particular set of diseases.

According to some embodiments, the training data comprises a ground-truth label of a corresponding analytical testing result. For example, a value "true" may indicate that the analytical testing result is labeled as valid e.g., by a medical professional. A value "false" may indicate that the analytical testing result is labeled as invalid e.g., by the medical professional According to some embodiments, during the training of the validation algorithm, a plurality of parameters of the validation algorithm, e.g., a plurality of weighting parameters of a neural network, may be iteratively adjusted based on a training object of the validation algorithm. For example, the training object of the validation algorithm may be determined based on a difference between the prediction result by the validation algorithm and the corresponding ground-truth label.

The validation algorithm may be deemed as converging when a variance of the training object in multiple iterations is for example less than a threshold. In this case, the validation algorithm would be deemed as trained, and the parameters in the last iteration would be considered as the final parameters of the trained validation algorithm. The trained validation algorithm would then be capable of validating an analytical testing result based on an input feature vector associated with the analytical testing result.

According to some embodiments, the first training data set may comprise real world data, i.e., the real-word analytical testing results and associated metadata. For example, the first training data set may comprise the plurality of analytical testing results generated in last year, and the ground-truth labels may be determined based on the feedbacks from the doctors.

According to some other embodiments, the first training data set may comprise artificial training data for enriching the training data set. For example, the artificial data may be generated by adjusting values of real-word data. By using artificial data, an over fitting problem of the validation algorithm may be avoided.

According the some embodiments, the training of the validation algorithm may be implemented by the monitoring system (20) itself, and the monitoring system (20) may then use the trained validation algorithm for validating an analytical testing result in the live data set.

According to some other embodiments, the training of the validation algorithm may be implemented by a different training system than the monitoring system (20). The monitoring system (20) may receive the trained validation algorithm from the training system, for example, through receiving the parameters of the trained validation algorithm from the training system. The monitoring system (20) may then deploy the trained validation algorithm according to the parameters automatically. Alternatively, the monitoring system (20) may be artificially deployed with the trained validation algorithm.

After the validation algorithm has been trained using the first training data set, the monitoring system (20) may use the trained validation algorithm to validate an analytical testing result. For ease of description, the trained validation algorithm herein may also be referred to as "the original validation algorithm" or "the first validation algorithm". According to some embodiments, the monitoring system (20) may first determine a feature vector based on the analytical testing data included in the live data set. Then the monitoring system (20) may apply the feature vector to the trained validation algorithm for invalidating the analytical testing result included in the analytical testing data.

At block 206, the monitoring system (20) evaluates a difference level between the live data set and the first training data set, wherein the difference level is determined based on distribution characteristics of the live data set and the first training data set. In some embodiments, a different level may indicate whether the live data set and the first training data set are similar. For example, a greater value of difference level may indicate a greater difference between the two data sets.

According to some embodiments, the monitoring system (20) may compare a first value indicative of the distribution characteristics of the first training data set and a second value indicative of the distribution characteristics of the live data set. According to some embodiments, the monitoring system (20) may determine the first and second values through a real-time calculation.

According to some other embodiments, the first value indicative of the distribution characteristics of the first training data set may be pre-determined and stored in a storage device (e.g. a disk or a memory) coupled to the monitoring system (20). During the comparison, the monitoring system (20) may obtain the value from the storage device without additional calculation.

According to some embodiments, the monitoring system (20) may periodically evaluate the difference level for determining whether a re-training of the validation algorithm is required. For example, the monitoring system (20) may evaluate the difference level every three months. Alternatively, the monitoring system (20) may evaluate the difference level after a predetermined number of samples have been processed.

According to some embodiments, the distribution characteristics of a data set represent a distribution of one or more aspects associated with the analyzer results. The distribution characteristics can be used to compare if two data sets represent analyzer testing data that have a similar distribution with respect to the chosen aspects. In an example, the aspect is the sex of the patients to which analyzer testing data is associated, and the distribution characteristics is the female share (in %) of said patients, and a difference level between a first data set and a second data set can e.g. be defined as the absolute value of the difference in the female share between the two data sets; and if this difference is too large, the two data sets are perceived as being too different. In an example, the female share of the live data set and the first training data is deemed to be too different, and the validation algorithm for validating the live data set is re-trained using a second training data set whose female share is closer to that of the live data set.

According to some embodiments, the distribution characteristic of a data set may be determined using a value of the analytical testing result included in the data set. For example, a distribution characteristic may comprise a highest value of the analytical testing results included in the data set.

In some other embodiments, the distribution characteristic of a data set may be determined using a value of each of the analytical testing results included in the data set. For example, a distribution characteristic may comprise an average value of all the analytical testing results. In some other examples, a distribution characteristic may comprise a variance of all the analytical testing results.

In this case, the monitoring system (20) may first determine a first value of the distribution characteristic of the live data set and determine a second value of the distribution characteristic of the first training data set. For example, the monitoring system (20) may determine that the average value of the analytical testing results in the live data set is "500", and determine that the average value of the analytical testing results in the first training data set is "300". In this case, the difference level may be determined as a value "200", which indicates a difference between the two average values.

According to some other embodiments, the distribution characteristic of a data set may also be determined using at least one aspect of the metadata associated with the analytical testing result included in the data set. For example, a distribution characteristic may comprise an average value or a variance of the ages of the patients associated with the analytical testing results in the data set.

Figure 3A:
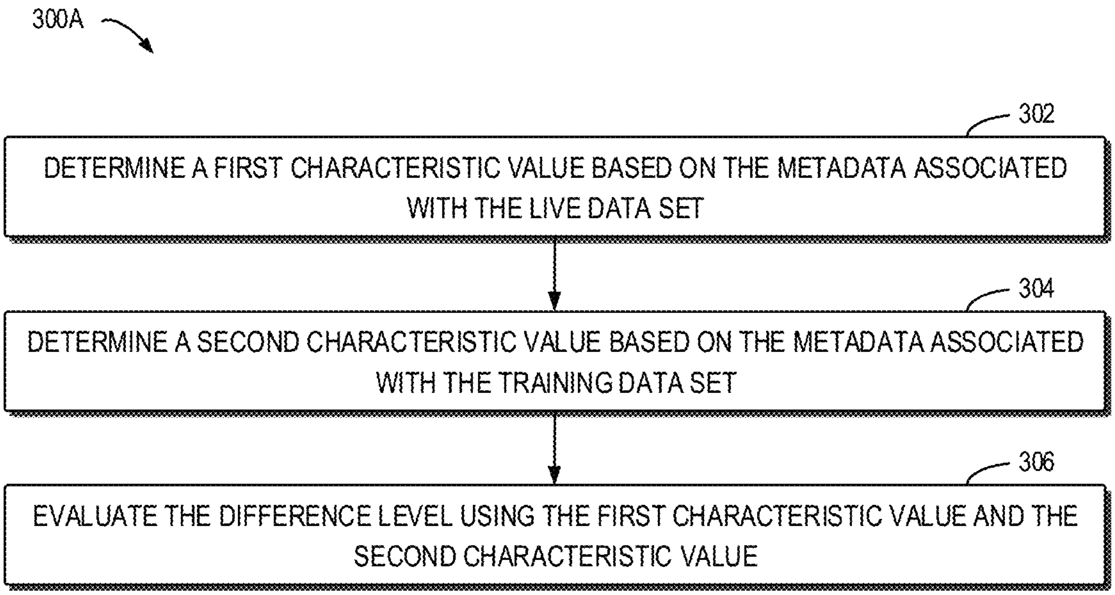
FIGS. 3A to 3C illustrate flowcharts of example processes of determining a difference level according to different implementations of the subject matter described herein.

According to some other embodiments, the difference level may be determined based on the values of at least one of the metadata included in the two data sets. Reference is now made to FIG. 3A, which illustrates a flowchart of example process 300A of determining a difference level according to some implementations.

As shown in FIG. 3A, at block 302, the monitoring system (20) may determine a first characteristic value based on metadata associated with the live data set.

According to some embodiments, the monitoring system (20) may determine the first characteristic value based on the values of the ages of the patients associated with the live data set. Examples of the first characteristic value may include but are not limited to: an average value of the ages of the patients, a variance of the ages, a percentage of old patients in the live data set, a highest value of the ages, a lowest value of the ages, a ratio of old patients to teenager patients, and the like.

According to some embodiments, the monitoring system (20) may determine the first characteristic value based on the gender of the patients associated with the live data set. Examples of the first characteristic value may include but are not limited to: a number of male patients in the live data set, a number of female patients in the live data set, a percentage of male patients in the live data set, a percentage of female patients in the live data set and the like.

According to some embodiments, the monitoring system (20) may determine the first characteristic value based on type of sources of the patients associated with the live data set. Examples of the first characteristic value may include but are not limited to: a number of patients who are in-patient in the live data set, a number of patients who are out-patient in the live data set, a percentage of patients who are in-patient in the live data set, a percentage of patients who are out-patient in the live data set and the like.

According to some embodiments, the monitoring system (20) may determine the first characteristic value based on wards of the patients associated with the live data set. Examples of the first characteristic value may include but are not limited to: a number of patients who are from a high-risk ward in the live data set, a number of patients who are not from a high-risk ward in the live data set, a percentage of patients who are from a high-risk ward in the live data set, a percentage of patients who are not from a high-risk ward in the live data set and the like.

According to some embodiments, the monitoring system (20) may determine the first characteristic value based on health diagnoses of the patients associated with the live data set. Examples of the first characteristic value may include but are not limited to: a number of patients whose diagnoses indicates a particular disease in the live data set, a number of patients whose diagnoses fails to indicate a particular disease in the live data set, a percentage of patients whose diagnoses indicates a particular disease in the live data set, a percentage of patients whose diagnoses fails to indicate a particular disease in the live data set and the like.

At block 304, the monitoring system (20) may determine a second characteristic value based on values of the at least one of metadata associated with the first training data set. It should be noted that the second characteristic value may be determined in a same way as discussed with regard to the first characteristic value.

According to some embodiments, the first characteristic value and the second characteristic value are each determined using a same characterization algorithm. For example, the first characteristic value and the second characteristic value are each determined using a same characterization algorithm of computing an average value.

Further, the characterization algorithm uses the one or more aspects of each metadata of each analytical testing data. For example, the same the one or more aspects may comprise at least one of the different aspects as discussed above: an age of a patient associated with the analytical testing result; a gender of the patient; a type of sourcing of the patient; a ward of the patient; and a health diagnosis of the patient.

According to some embodiments, the second characteristic value may be pre-determined and then maintained in a storage device coupled to the monitoring system (20). In this case, the monitoring system (20) may retrieve the second characteristic value from the storage device, and no additional calculation would be required.

At block 306, the monitoring system (20) may evaluate the difference level using the first characteristic value and the second characteristic value. According to some embodiments, the monitoring system (20) may determine the difference level using a difference value between the first characteristic value and the second characteristic value.

In some cases, the difference level may comprise the difference value itself. In some other cases, the difference level may also be determined by comparing the difference value with particular value ranges. For example, if a difference value falls into a value range "100-199", the difference level may be set as "1"; and if a difference value falls into a value range "200-299", the difference level may be set as "2".

Alternatively, the monitoring system (20) may also determine the difference level using a ratio of the first characteristic value and the second characteristic value. For example, if the first characteristic value is "400" and the second characteristic value is "200", the difference level may then be determined as "2".

By determining the difference level between the live data set and the first training data set based on the metadata, the monitoring system may determine whether the live data set is similar to the first training data set, thereby facilitating autonomous triggering of re-training of the validation algorithm.

Figure 3B:
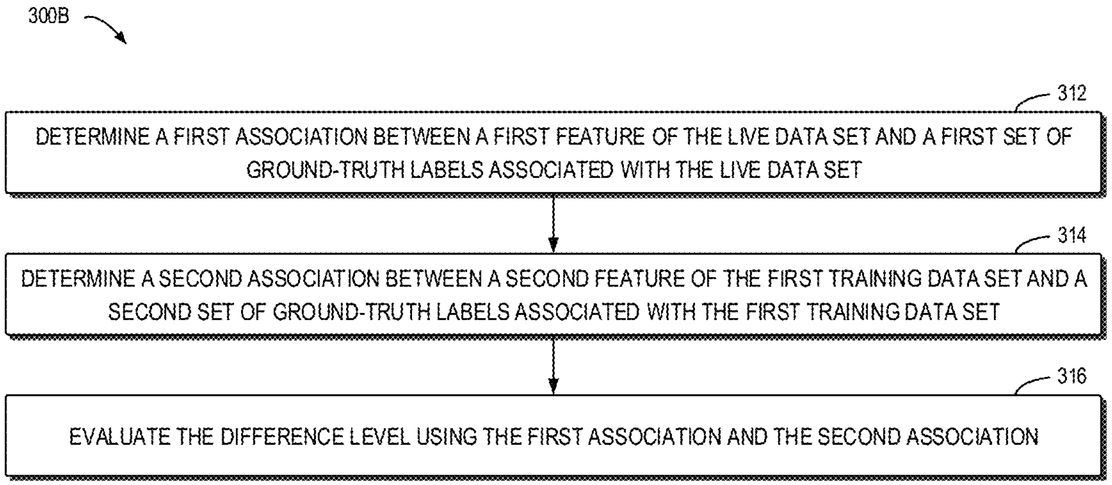

According to some other embodiments, the difference level may also be determined based on the contribution of the features included in the feature vector to the ground-truth label. Reference is now made to FIG. 3B, which illustrates a flowchart of example process 300B of determining a difference level according to some other implementations.

As shown in FIG. 3B, at block 312, the monitoring system (20) may determine a first association between a first feature of the live data set and a first set of ground-truth labels associated with the live data set, wherein the first set of ground-truth labels are indicative of a validity value of each of the plurality of analytical testing data included in the live data set.

According to some embodiments, a validity value may be an assigned value. For example, the validity value may be assigned by a medical professional after evaluating the respective analytical testing result. A validity value "1" may for example indicate that the analytical testing result is objectively valid, and a validity value "0" may indicate that the analytical testing result is objectively invalid. It should be understood that, a validity value herein is not set by the validation algorithm.

According to some embodiments, the monitoring system (20) may apply a Random Forests model to determine the first association, e.g., a correlation, between the first feature and the ground-truth labels. The first feature may comprise at least one of: a value of an analytical testing result and one or more aspects of metadata of each analytical testing data.

According to some embodiments, the first association between the first feature of the live data set and the first set of ground-truth labels associated with the live data set is determined using an association algorithm; and the second association second feature of the first training data set and the second set of ground-truth labels associated with the first training data set is also determined using the same association algorithm.

According to some embodiments, the association is an indicator of a correlation between a certain feature, e.g. a patient having a certain medical diagnosis, and the validity value of a ground-truth label, which can e.g. represent that an analytical testing result should have been deemed valid resp. invalid. The association can e.g. be expressed by a correlation coefficient between 0 and 1. In an example, the difference between a) the correlation between a certain feature and the truth values for the live data set and b) the correlation between this certain feature and the truth values for the first training set is bigger than the difference between a) the correlation between this certain feature and the truth values for the live data set and c) the correlation between this certain feature and the truth values for the second training set, and the validation algorithm is re-trained using the second training set.

In particular, the monitoring system (20) may use the feature vectors associated with the live data set and the first set of ground-truth labels for training the Random Forest model. After the Random Forest model has been trained, the Random Forest model could provide a contribution of the first to the final result (e.g., valid or invalid based on the ground-truth label). It should be understood that a higher contribution means that this feature plays a more important role in the association of the input feature vector and the ground-truth label.

At block 314, the monitoring system (20) may determine a second association, e.g., a correlation, between a second feature of the first training data set and a second set of ground-truth labels associated with the first training data set, wherein the second set of ground-truth labels are indicative of a validity value of each of the plurality of training analytical testing data included in the first training data set. According to some embodiments, the second feature may comprise at least one of: a value of an analytical testing result and a same aspect of each metadata of each analytical testing data.

According to some embodiments, the monitoring system (20) may determine the second association in a similar way as block 312. According to some other embodiments, the second association may be pre-determined by another entity and maintained in a storage device coupled to the monitoring system (20). In this case, the monitoring system (20) may directly retrieve the second association from the storage device, without requiring any additional calculation.

At block 316, the monitoring system (20) may evaluate the difference level using the first association and the second association. In some embodiments, the monitoring system (20) may compares a first ranking of a first association of a particular feature and a second ranking of a second association of the particular feature.

For example, the monitoring system (20) may determines that the feature "ward" has a largest contribution based on the live data set and has a second contribution which ranks in a 5th place according to the first training data set. In this case, the difference level may be determined as the difference between the two ranks.

In another example, the monitoring system (20) may determine a first relative ranking of contributions of at least two features based on the live data set, and determine a second relative ranking based on the first training data set.

For example, the monitoring system (20) may determine that the feature "ward" has a largest contribution and the feature "gender" has a $5^{th}$ largest contribution based on the live data set. Then the monitoring system (20) may determine that the first relative ranking of the feature "ward" and the feature "gender" is "+4" based on the live data set. Similarly, the monitoring system (20) may determine that the feature "ward" has a $6^{th}$ largest contribution and the feature "gender" has a $2^{nd}$ largest contribution based on the first training data set. Then the monitoring system (20) may determine that the first relative ranking of the feature "ward" and the feature "gender" is "−4" based on the first training data set.

In this case, the monitoring system (20) may further determine the difference level based on the first relative ranking and the second relative ranking. For example, the difference level may be determined as "8" if the first relative ranking is "+4" and the second relative ranking is "−4".

According to some embodiments, the monitoring system (20) may consider the contribution of each of the features (e.g., analytical testing result, age, gender, type of source, ward and health diagnosis) in the feature vector. For example, the monitoring system (20) may determine a rank difference of each of the features based on the live data set and the training data set, and then use e.g. a sum of the rank differences to determine the difference level.

Figure 3C:
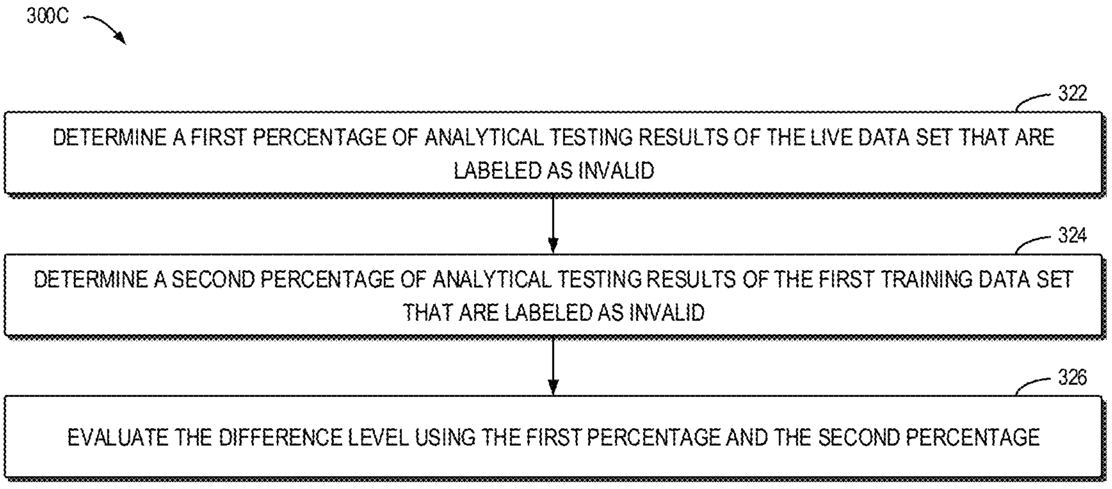

According to some further embodiments, the difference level may also be determined based on a percentage of analytical testing results that are labeled as invalid, e.g. according to a ground-truth label that has been assigned to the analytical testing result e.g. by a medical and/or laboratory professional. Reference is now made to FIG. 3C, which illustrates a flowchart of example process 300C of determining a difference level according to some other implementations.

As shown in FIG. 3C, at block 322, the monitoring system (20) may determine a first percentage of analytical testing results of the live data set that are labeled as invalid. According to some embodiments, an analytical testing result that is labeled as invalid may be determined according to the first set of ground-truth labels associated with the live data set. As discussed above, the first set of ground-truth labels are indicative of a validity value of each of the plurality of analytical testing data included in the live data set. For example, a validity value "0" may indicate that the corresponding analytical testing result is labeled as invalid.

According to some embodiments, the monitoring system (20) may determine, based on the first set of ground-truth labels associated with the live data set, how many analytical testing results are labeled as invalid in the live data set. For example, the monitoring system (20) may determine that 20% of the analytical testing results are labeled as invalid in the live data set.

At block 324, the monitoring system (20) may determining a second percentage of analytical testing results of the first training data set that are labeled as invalid. Similarly, an analytical testing result that is labeled as invalid may be determined according to the second set of ground-truth labels associated with the first training data set. As discussed above, the second set of ground-truth labels are indicative of a validity value of each of the plurality of analytical testing data included in the first training data set.

According to some embodiments, the monitoring system (20) may determine, based on the second set of ground-truth labels associated with the first training data set, how many analytical testing results are labeled as invalid in the live data set. For example, the monitoring system (20) may determine that 5% of the analytical testing results are labeled as invalid in the first training data set.

According to some embodiments, the second percentage may also be pre-determined and stored in a storage device coupled to the monitoring system (20). The monitoring system (20) may therefore directly retrieve a value indicative of the second percentage from the storage device, thereby avoiding unnecessary re-calculation.

At block 326, the monitoring system (20) may evaluate the difference level using the first percentage and the second percentage. According to some embodiments, the monitoring system (20) may determine the difference level using the difference between the first percentage and the second percentage. For example, the monitoring system (20) may determine the difference level as "15%" when the first percentage is "20%" and the second percentage is "5%".

According to some further embodiments, evaluating a difference level between two data sets, e.g. between a live data set and a training set, can comprise a cluster analysis. According to some specific embodiments, the two data sets are deemed part of a set of data sets and the cluster analysis is performed on this set of data sets. In an example, the cluster analysis provides a distance of the two data sets in the set of data sets and the distance can be used for calculating the difference level between the two data sets.

Reference is now made again to FIG. 2, at block 208, the monitoring system (20) compares the difference level with a first threshold. If it is determined that the difference level is not greater than the threshold, the process 200 proceeds to block 214. At block 214, the monitoring system (20) continues using the validation algorithm for future validation of an analytical testing result, and no re-training would be required.

According to some embodiments, the first threshold is static. The static value of the first threshold can e.g. predefined by a user. In this manner, the user can influence the sensitivity of the re-training procedure.

According to some embodiments, the first threshold is dynamic. In an example, the first threshold is a difference level between the live data set and another training set. According to some specific embodiments, the re-training is made if the difference level between the live data set and the first training set is greater than the difference level between the live data set and the another training set, wherein the difference level in each case is determined in a same manner. The another training data set could be a second training data set that later can be used for re-training the validation algorithm.

According to some embodiments, the first threshold comprises a static component and a dynamic component, e.g. wherein the first threshold comprises a first static value and a second dynamic value to which a difference level comprising two values is to be compared.

In contrast, if it is determined that the difference level is greater than the threshold, the process 200 proceeds to block 210. At block 210, the monitoring system (20) re-trains the validation algorithm using a second training data set different from the first training data set.

When the different level is greater than the threshold, it may indicate that the live data set is now greatly different from the training data set. In this case, the validation algorithm is now error prone and re-training of the validation algorithm is required. For example, if the validation algorithm is trained using a plurality of historical analytical testing data generated from a hospital, and a great difference level would then be found when using the validation algorithm to process analytical testing data generated from a different hospital. In this case, re-training of the validation algorithm is required.

It should be understand that the term "greater" here is a representation of a comparison, and that an actual operation can also be being mathematically lower than a numerical threshold.

According to some embodiments, wherein the step of re-training of the validation algorithm is only conducted if an additional condition is met. For example, the monitoring system (20) may request a confirmation from a user for the retraining and may then conduct the re-training after receiving the confirmation from the user. In another example, the monitoring system (20) may determine whether there are sufficient computing resources for the re-training available and the re-training is initiated when determining that there are sufficient computing resources available.

According to some embodiments, the re-training step may be automatically triggered without meeting an additional condition.

According to some embodiments, the second training data set may be selected from a group of training data sets, such that a difference level between the live data set and the second training data set is lower than a second threshold. In this way, the re-trained validation algorithm may have a better performance for processing analytical testing data. It should be understood that the term "lower" here is a representation of comparison and is used here to express that it is opposed to the notion of "greater" for the first threshold. The second threshold can be static and/or dynamic, e.g. it can comprise a static component and a dynamic component. According to some specific embodiments, the difference level between the live data set and the first training set and the difference level between the live data set and the second training set are determined using a same difference level algorithm.

According to some embodiments, the second training data set may comprise the live data set. For example, the monitoring system (20) may use the live data set the corresponding ground-truth labels to re-train the validation algorithm. In some embodiments, the monitoring system (20) may update the validation algorithm by adjusting the parameters included therein based on the live data set. In this way, the re-trained validation algorithm may achieve a good performance for both the first training data set as well as the live data set. For ease of description, the re-trained validation algorithm is also referred to as "a second validation algorithm".

According to some other embodiments, the monitoring system (20) may also re-train cause a completely new validation algorithm, e.g., an initial neural network, using the live data set and other training data set.

In a practical example, the difference level between a live data set and a first training set is evaluated using a cluster analysis, and no re-training is performed if—as a result of the cluster analysis—the live data set and the first training set are deemed to belong to a same cluster, and re-training is performed if—as a result of the cluster analysis—the live data set and the first training set are deemed to belong to different clusters.

At block 212, the monitoring system (20) uses the re-trained validation algorithm for future validation of an analytical testing result. For example, a feature vector may be determined when receiving a new analytical testing data, and may then then applied to the re-trained validation algorithm for validating the analytical testing result.

Through the process discussed above, the embodiments of the present disclosure may automatically trigger the re-training of the validation algorithm when determining that the live data set being currently processed is sufficiently different from the first training data set used to train the validation algorithm.

Figure 4:
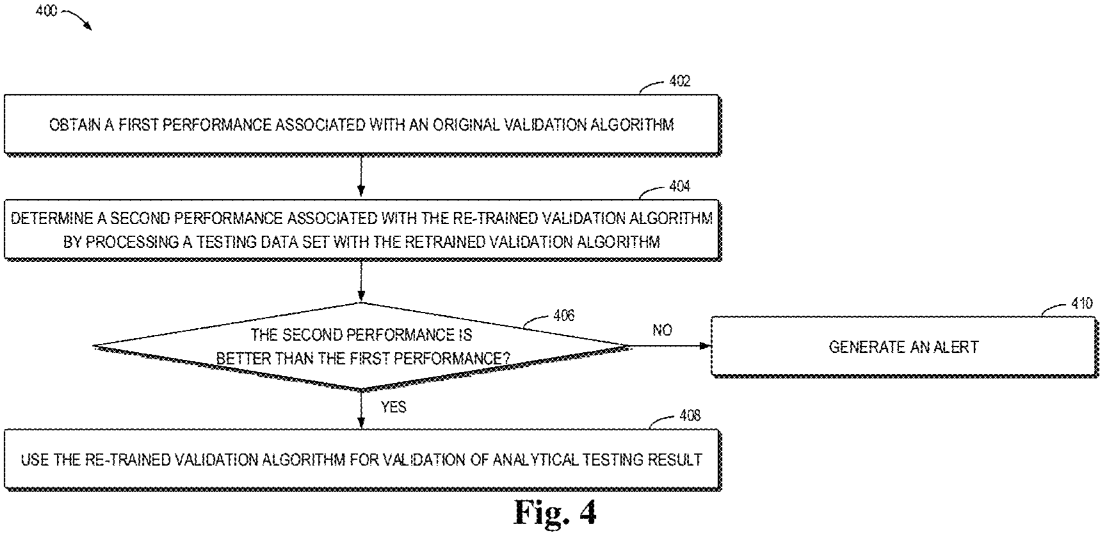
FIG. 4 illustrates a flowchart of a process of using the re-trained validation algorithm according to an implementation of the subject matter described herein.

According to some embodiments, the re-trained validation algorithm is used for future validation of an analytical testing result only if a performance condition is met. Such a performance condition can e.g. be that a first performance associated with the original validation algorithm is worse than a second performance associated with the re-trained validation algorithm. FIG. 4 illustrates a flowchart of a process (400) of using the re-trained validation algorithm according to an implementation of the subject matter described herein.

As shown in FIG. 4, at block 402, the monitoring system (20) may obtain a first performance associated with the original validation algorithm. In some embodiments, the first performance associated with the original validation algorithm (i.e., the first validation algorithm) may be determined by processing a testing data set using the original validation algorithm. In some embodiments, the testing data set may for example comprise a benchmark testing data set, which includes a plurality of analytical testing data.

At block 404, the monitoring system (20) may determine a second performance associated with the re-trained validation algorithm by processing a testing data set with the re-trained validation algorithm.

Figure 5A:
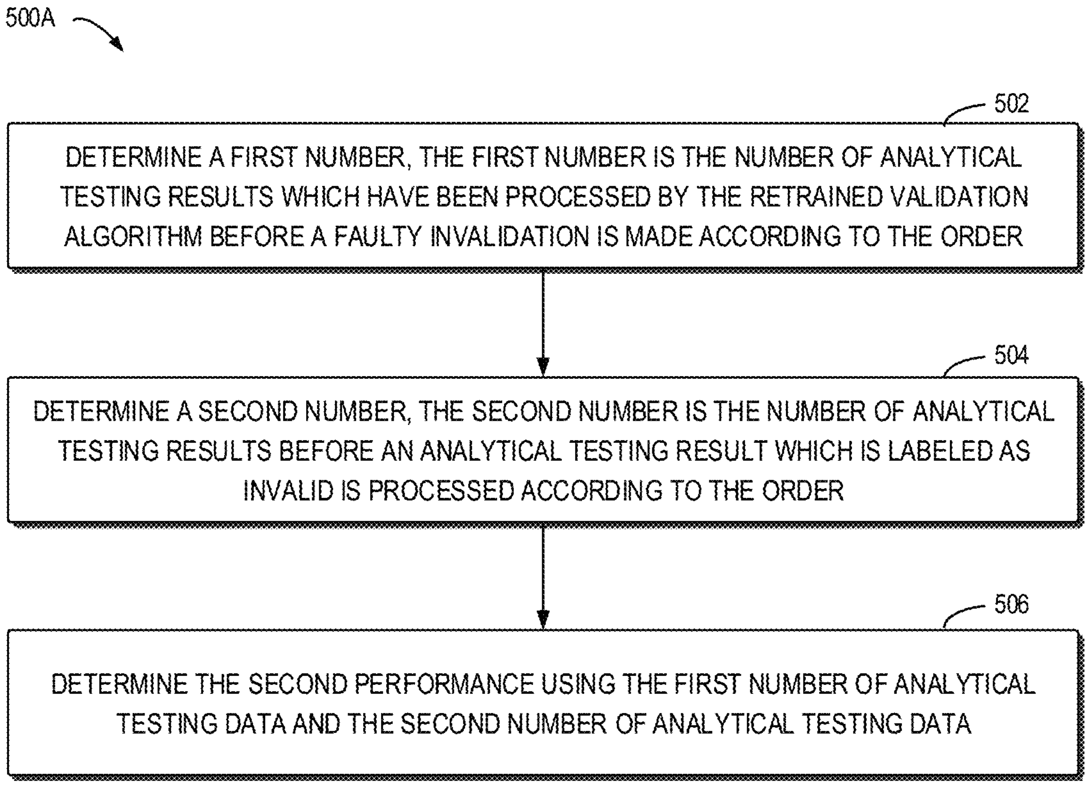
FIGS. 5A to 5B illustrate flowcharts of example processes of determining a performance of the re-trained validation algorithm according to different implementations of the subject matter described herein.

According to some embodiments, the training data set may be processed by the re-trained validation algorithm according to an order, and the second performance may be determined based on a number of analytical testing results before a faulty prediction. FIG. 5A illustrates a flowchart of a process (500A) of determining a performance of the re-trained validation algorithm according to different implementations of the subject matter described herein.

As show in FIG. 5A, at block 502, the monitoring system (20) may determine a first number, wherein the first number is the number of analytical testing results that have been processed by the re-trained validation algorithm before a faulty invalidation is made by the re-trained validation algorithm according to the order. Herein, a faulty invalidation means that the validation algorithm incorrectly determines that an analytical testing result is invalid although this analytical testing result is labeled as valid according to a ground-truth label. For example, the monitoring system (20) may determine that thirty-five analytical testing results have been processed by the validation system before a faulty invalidation is made according to the order.

At block 504, the monitoring system (20) may determine a second number, wherein the second number is the number of analytical testing results before an analytical testing result that is labeled as invalid is processed according to the order. For example, the monitoring system (20) may determine, based on the corresponding set of ground-truth labels, that twenty analytical testing results have been processed before the analytical testing result that is labeled as invalid.

At block 506, the monitoring system (20) may determine the second performance using the first number of analytical testing data and the second number of analytical testing data. According to some embodiments, the monitoring system (20) may use a difference value between the first number of analytical testing results and the second number of analytical testing results as the performance metric (also referred to as a first performance metric), a performance metric being a quantification of a performance. For example, the second performance could be determined as "fifteen" if a value of the first number is "thirty-five" and a value of the second number is "twenty". It should be understood that, a lower numerical value of the first performance metric in this case indicates a poorer performance. However, it is of course conceivable to define other performance metrics where a higher numerical value indicates a poorer performance (e.g. the inverse of performance metric described before.

Figure 5B:
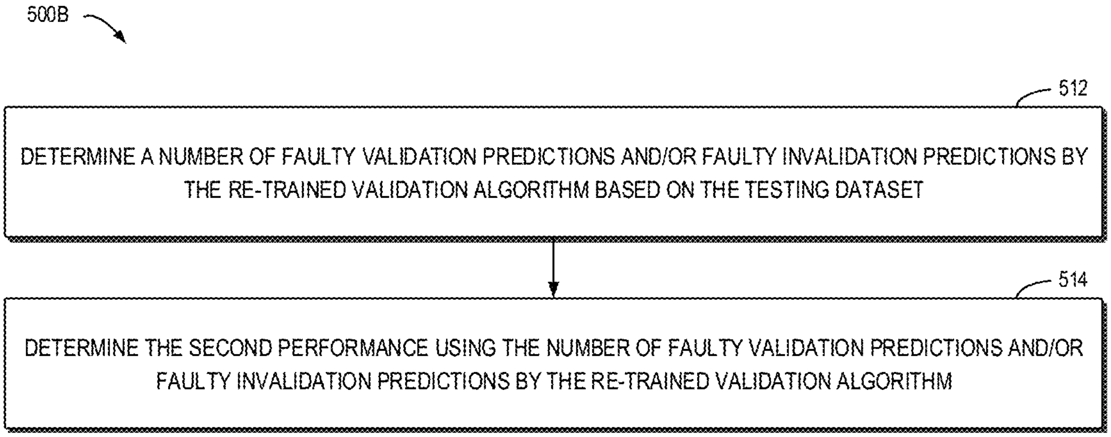

According to some embodiments, the second performance may be determined based on a number of faulty predictions. FIG. 5B illustrates a flowchart of a process (500B) of determining a performance of the re-trained validation algorithm according to different implementations of the subject matter described herein.

As shown in FIG. 5B, at block 512, the monitoring system (20) may determine a number of faulty validation predictions and/or faulty invalidation predictions by the re-trained validation algorithm based on the testing data set. Herein, a faulty validation prediction means that the validation algorithm incorrectly determines that an analytical testing result, which is labeled as invalid according to a ground-truth label, is valid. A faulty invalidation prediction means that the validation algorithm incorrectly determines that an analytical testing result, which is labeled as valid according to a ground-truth label, is invalid.

According to some embodiments, the monitoring system (20) may only determine the number of faulty validation predictions. According to some other embodiments, the monitoring system (20) may only determine the number of faulty invalidation predictions. According to some further embodiments, the monitoring system (20) may determine both the number of faulty validation predictions and the number of invalidation predictions, and e.g. further calculates the sum of the number of faulty validation predictions and the number of invalidation predictions.

At block 514, the monitoring system (20) may determine the second performance using the number of faulty validation predictions and/or faulty invalidation predictions by the re-trained validation algorithm. For example, the monitoring system (20) may only use the number of faulty validation predictions as a metric for the second performance. Alternatively, the monitoring system (20) may only use the number of faulty invalidation predictions as a metric for the second performance. In some other instances, the monitoring system (20) may also use the sum of both numbers as a metric for the second performance. Such kind of metrics may also be referred to as a second performance metric. It should be understood that, a lower value of the second performance metric indicates a better performance.

According to some embodiments, the monitoring system (20) may use a combination of the different performance metrics as discussed above. For example, a weighed sum of the first and second performance metrics may be used for determining the second performance.

Reference is made again to FIG. 4, at block 406, the monitoring system (20) may compare the first performance with the second performance. If the second performance is not better than the first performance, the process (400) may proceed to block 410. At block 410, the monitoring system (20) may not automatically deploy the re-trained validation algorithm, but e.g. generate an alert for indicating that the original validation algorithm needs to be re-trained but the autonomous re-training of the validation algorithm is not good enough and/or re-train the validation algorithm using a different (e.g. a third) training data set.

In contrast, if it is determined that the second performance is better than the first performance, the process (400) may proceed to block 408. At block 408, the monitoring system (20) may use the re-trained validation algorithm for future validation of an analytical testing result.

According to some embodiments, an analytical testing result that is deemed invalid by the validation algorithm (the first validation algorithm or the second validation algorithm) is flagged in a databank, which can allow users to know about the failed validation.

According to some embodiments, if an analytical testing result is deemed invalid by the validation algorithm, the analytical testing result is evaluated by a human, e.g. a health-care professional. According to some specific embodiments, the human provides feedback, e.g. if the analytical testing result should have been validated, e.g. because it is deemed acceptable by the human. A respective system can comprise an interface that a human can use for entering feedback. The feedback can e.g. be used for (re-) training the validation algorithm.

According to some embodiments, the analytical testing is repeated if an analytical testing result is deemed invalid by the validation algorithm.

According to some embodiments, an analysis of the analytical testing results and the results of the validation algorithm may be performed. According to some specific embodiments, the analysis comprises performing an analysis of the analytical testing results that are deemed as invalid by the validation algorithm. For example, a monitoring system may calculate how many analytical testing data that are deemed as invalid in a predetermined time, and/or a number of consecutive analytical testing data that are deemed as invalid. The analysis may comprise finding patterns in the analytical testing results being deemed invalid by the validation algorithm, e.g. a common instrument and/or a common person being part of determining said analytical testing results. The analysis may comprise determining a correlation of one or more aspects of the metadata and analytical testing results that are deemed as invalid by the validation algorithm, which can allow for determining of a possible source of errors that e.g. may be specific to patients with certain features related to these aspects. The analysis can comprise a statistical analysis.

According to some embodiments, information relating to the analysis and/or statistics may be displayed on a screen to a user. The display may comprise a dashboard and/or graphs. The displayed information can be accumulated e.g. according to different analyzers, medical practitioners, wards and/or lots.

According to some embodiments, the monitoring system may inform a user (e.g. a user of the monitoring system, of the analyzer instrument, of a middleware, of a HIS, and/or of a LIS) of a possible error of the analyzing testing process, e.g. based on the analysis. For example, when a number of analytical testing data that are deemed as invalid in a morning is exceeding a threshold, the monitoring system may generate an informing of a possible error of the analyzing testing process performed in that morning. The informing can comprise indicating a respective signal to a user, e.g. by sending a message to a device, by displaying a message on a device, and/or by voicing a message by a device. The indicated signal can e.g. comprise information on the error, e.g. which analyzers, which lots, and/or which personnel are associated with the error.

According to some specific embodiments, the analytical testing results are provided by an analyzer instrument and the monitoring system is designed for informing a user of the analyzer instrument of a possible error associated with the analyzer instrument based on the analysis.

According to some embodiments, the validation algorithm may comprise a first algorithm and a second algorithm. Both of the first and second algorithms may be configured to receive the feature vector associated with the analytical testing result, and output a prediction whether the analytical testing result is valid.

According to some embodiment, the first algorithm and the second algorithm are trained such that the first algorithm is stricter than the second algorithm with respect to validating analytical testing data. "Stricter" here can e.g. mean the share of analytical testing data of a specific data set that is deemed invalid by the first algorithm is greater than the share of analytical testing data of this specific data set that is deemed invalid by the second algorithm, e.g. wherein the specific data set with which the current validation algorithm is trained may be a testing data set, and/or a standardized data set. In some embodiments, the first algorithm and the second algorithm may be implemented using neural network model with a same structure. The hyper-parameters of the first algorithm and the second algorithm may be adjusted, such that the first algorithm could have a lower false positive rate than the second algorithm. Herein, a false positive prediction means that the validation algorithm incorrectly deems an analytical testing result as valid although it is labeled as invalid, e.g. by a medical professional.

Figure 6:
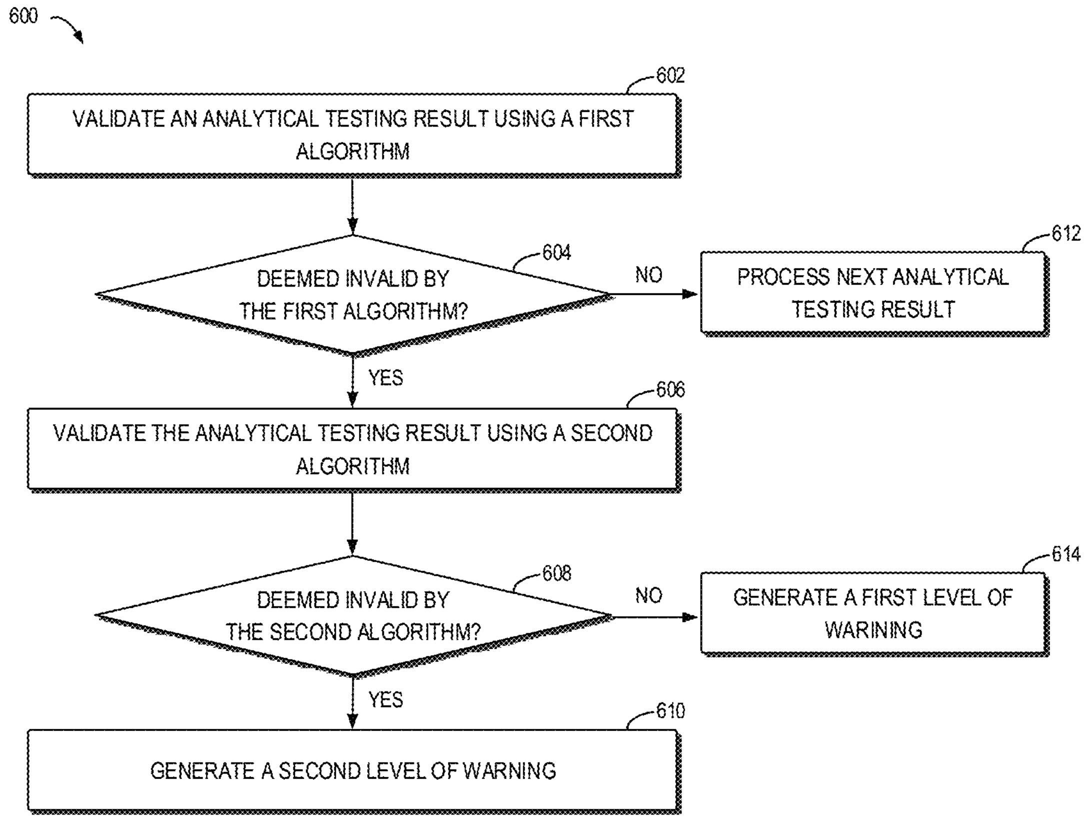
FIG. 6 illustrates a flowchart of a process of generating a warning by the validation algorithm according to an implementation of the subject matter described herein.

According to some embodiments, the first algorithm and the second algorithm may be used to generate different levels of warnings. FIG. 6 illustrates a flowchart of a process (600) of generating a warning by the validation algorithm according to an implementation of the subject matter described herein.

As shown in FIG. 6, at block 602, the monitoring system (20) may validate an analytical testing result using the first algorithm. For example, the feature vector associated with the analytical testing result may be applied to the first algorithm.

At block 604, the monitoring system (20) determines whether the analytical testing result is deemed invalid by the first algorithm. If no, the process (600) may proceed to block 612. At block 612, the monitoring system (20) may process a next analytical testing result.

If it is determined that the analytical testing result is deemed invalid by the first algorithm, the process (600) may proceed to block 606. At block 606, the monitoring system (20) may validate an analytical testing result using the second algorithm. In other words, the second algorithm processes the analytical testing data only if the analytical testing result is deemed invalid by the first algorithm. For example, the feature vector associated with the analytical testing result may be applied to the second algorithm.

At block 608, the monitoring system (20) determines whether the analytical testing result is deemed invalid by the second algorithm. If no, the process (600) may proceed to block 614. At block 614, the monitoring system (20) may generate a first level of warning.

If it is determined that the analytical testing result is deemed invalid by the second algorithm, the process (600) may proceed to block 610. At block 600, the monitoring system (20) may generate a first level of warning.

According to some embodiment, the second level of warning may indicate a higher seriousness than the first level of warning. For example, the second level of warning may use a brighter color, a louder sound, and/or a greater vibration than the first level of warning.

In such a way, the monitoring system (20) could provide different levels of warnings, thereby avoiding unnecessary interruption caused by incorrect warnings.

Figure 7:
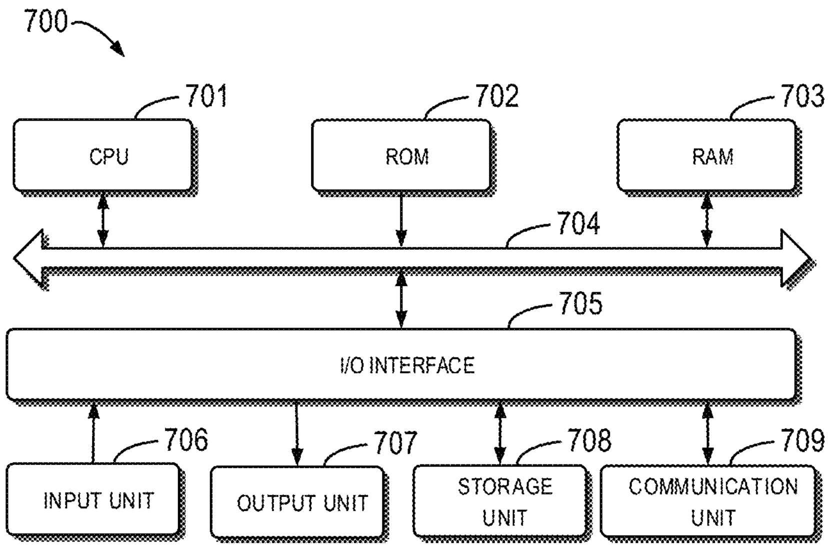
FIG. 7 illustrates a schematic block diagram of an example device for implementing embodiments of the present disclosure.

FIG. 7 illustrates a schematic block diagram of an example device 700 for implementing embodiments of the present disclosure. For example, the monitoring system (20) according to the embodiment of the present disclosure can be implemented by the device 700. As shown, the device 700 includes a central processing unit (CPU) 701, which can execute various suitable actions and processing based on the computer program instructions stored in a read-only memory (ROM) 702 or computer program instructions loaded in a random-access memory (RAM) 703 from a storage unit 708. The RAM 703 may also store all kinds of programs and data required by the operations of the device 700. The CPU 701, ROM 702 and RAM 703 are connected to each other via a bus 704. The input/output (I/O) interface 705 is also connected to the bus 704.

A plurality of components in the device 700 is connected to the I/O interface 705, including: an input unit 706, for example, a keyboard, a mouse, and the like; an output unit 707, for example, various kinds of displays and loudspeakers, and the like; a storage unit 708, such as a magnetic disk and an optical disk, and the like; and a communication unit 709, such as a network card, a modem, a wireless transceiver, and the like. The communication unit 709 allows the device 700 to exchange information/data with other devices via the computer network, such as Internet, and/or various telecommunication networks.

The above described process and processing, for example, the process 200, can also be performed by the processing unit 701. For example, in some embodiments, the process 200 may be implemented as a computer software program being tangibly included in the machine-readable medium, for example, the storage unit 708. In some embodiments, the computer program may be partially or fully loaded and/or mounted to the device 700 via the ROM 702 and/or communication unit 709. When the computer program is loaded to the RAM 703 and executed by the CPU 701, one or more steps of the above described methods or processes can be implemented.

The present disclosure may be a method, a device, a system and/or a computer program product. The computer program product may include a computer-readable storage medium, on which the computer-readable program instructions for executing various aspects of the present disclosure are loaded.

The computer-readable storage medium may be a tangible device that maintains and stores instructions utilized by the instruction executing devices. The computer-readable storage medium may be, but is not limited to, an electrical storage device, a magnetic storage device, an optical storage device, an electromagnetic storage device, a semiconductor storage device or any appropriate combination of the above. More concrete examples of the computer-readable storage medium (non-exhaustive list) include: a portable computer disk, a hard disk, a random-access memory (RAM), a read-only memory (ROM), an erasable programmable read-only memory (EPROM or flash), a static random-access memory (SRAM), a portable compact disk read-only memory (CD-ROM), a digital versatile disk (DVD), a memory stick, a floppy disk, a mechanical coding device, a punched card stored with instructions thereon, or a projection in a slot, and any appropriate combination of the above. The computer-readable storage medium utilized herein is not interpreted as transient signals per se, such as radio waves or freely propagated electromagnetic waves, electromagnetic waves propagated via waveguide or other transmission media (such as optical pulses via fiber-optic cables), or electric signals propagated via electric wires.

The described computer-readable program instructions may be downloaded from the computer-readable storage medium to each computing/processing device, or to an external computer or external storage via Internet, local area network, wide area network and/or wireless network. The network may include copper-transmitted cables, optical fiber transmissions, wireless transmissions, routers, firewalls, switches, network gate computers and/or edge servers. The network adapter card or network interface in each computing/processing device receives computer-readable program instructions from the network and forwards the computer-readable program instructions for storage in the computer-readable storage medium of each computing/processing device.

The computer program instructions for executing operations of the present disclosure may be assembly instructions, instructions of instruction set architecture (ISA), machine instructions, machine-related instructions, microcodes, firmware instructions, state setting data, or source codes or target codes written in any combination of one or more programming languages, where the programming languages consist of object-oriented programming languages, e.g., Smalltalk, C++, and so on, and conventional procedural programming languages, such as "C" language or similar programming languages. The computer-readable program instructions may be implemented fully on a user computer, partially on the user computer, as an independent software package, partially on the user computer and partially on a remote computer, or completely on the remote computer or a server. In the case where a remote computer is involved, the remote computer may be connected to the user computer via any type of network, including a local area network (LAN) and a wide area network (WAN), or to the external computer (e.g., connected via Internet using an Internet service provider). In some embodiments, state information of the computer-readable program instructions is used to customize an electronic circuit, e.g., a programmable logic circuit, a field programmable gate array (FPGA) or a programmable logic array (PLA). The electronic circuit may execute computer-readable program instructions to implement various aspects of the present disclosure.

Various aspects of the present disclosure are described herein with reference to a flow chart and/or block diagram of method, device (system) and computer program products according to embodiments of the present disclosure. It should be appreciated that each block of the flow chart and/or block diagram and the combination of various blocks in the flow chart and/or block diagram can be implemented by computer-readable program instructions.

The computer-readable program instructions may be provided to the processing unit of a general-purpose computer, dedicated computer or other programmable data processing devices to manufacture a machine, such that the instructions, when executed by the processing unit of the computer or other programmable data processing apparatuses, generate an apparatus for implementing functions/actions stipulated in one or more blocks in the flow chart and/or block diagram. The computer-readable program instructions may also be stored in the computer-readable storage medium and cause the computer, programmable data processing apparatus and/or other devices to work in a particular manner, such that the computer-readable medium stored with instructions contains an article of manufacture, including instructions for implementing various aspects of the functions/actions stipulated in one or more blocks of the flow chart and/or block diagram.

The computer-readable program instructions may also be loaded into a computer, other programmable data processing apparatuses or other devices, so as to execute a series of operation steps on the computer, other programmable data processing apparatuses or other devices to generate a computer-implemented procedure. Therefore, the instructions executed on the computer, other programmable data processing apparatuses or other devices implement functions/actions stipulated in one or more blocks of the flow chart and/or block diagram.

The flow chart and block diagram in the drawings illustrate system architectures, functions and operations that may be implemented by a system, a method and a computer program product according to multiple implementations of the present disclosure. In this regard, each block in the flow chart or block diagram can represent a module, a portion of program segment or code, where the module and the portion of program segment or code include one or more executable instructions for performing stipulated logic functions. In some alternative implementations, it should be appreciated that the functions indicated in the block may also take place in an order different from the one indicated in the drawings. For example, two successive blocks may be in fact executed in parallel or sometimes in a reverse order depending on the involved functions. It should also be appreciated that each block in the block diagram and/or flow chart and combinations of the blocks in the block diagram and/or flow chart may be implemented by a hardware-based system exclusively for executing stipulated functions or actions, or by a combination of dedicated hardware and computer instructions.

Various implementations of the present disclosure have been described above and the above description is only exemplary rather than exhaustive and is not limited to the implementations of the present disclosure. Many modifications and alterations, without deviating from the scope and spirit of the explained various implementations, are obvious for those skilled in the art. The selection of terms in the text aims to best explain principles and actual applications of each implementation and technical improvements made in the market by each embodiment, or enable others of ordinary skill in the art to understand implementations of the present disclosure.

The following embodiments are proposed:

Proposal 1. A diagnostic analyzing system (1), comprising:

one or more analyzer instruments (10) designed for providing an analytical testing result;

a monitoring system (20) designed for processing an analytical testing data, the analytical testing data comprising an analytical testing result provided by the one or more analyzer instruments (10) and metadata associated with the analytical testing result, the monitoring system (20) being designed for validating an analytical testing result using a validation algorithm, the validation algorithm being trained using a first training data set comprising a plurality of training analytical testing data, each training analytical testing data comprising a training analytical testing result and training metadata, and the monitoring system (20) being designed for evaluating a difference level between a live data set of analytical testing data and the first training data set, the difference level being determined based on a comparison of distribution characteristics of the live data set and the first training data set, and re-training the validation algorithm using a second training data set if the difference level between the live data set and the first training data set is greater than a first threshold, and using the re-trained validation algorithm for validation of an analytical testing result.

Proposal 2. The diagnostic analyzing system of Proposal 1, wherein a difference level between the live data set and the second training data set is lower than a second threshold.

Proposal 3. The diagnostic analyzing system of any of the preceding Proposals, wherein the second training data set comprises the live data set.

Proposal 4. The diagnostic analyzing system of any of the preceding Proposals, wherein the monitoring system (20) is designed for:

performing an analysis of the analytical testing results and the results of the validation algorithm.

Proposal 5. The diagnostic analyzing system of Proposal 4, wherein the monitoring system (20) is designed for informing a user of the monitoring system (20) of a possible error associated with the analyzing testing process based on the analysis.

Proposal 6. The diagnostic analyzing system of any of the preceding Proposals, wherein at least one of the one or more analyzer instruments (10) is a biological sample analyzer designed for processing biological samples and providing an analytical testing result associated with the biological sample.

Proposal 7. The diagnostic analyzing system of any of the preceding Proposals, wherein at least one of the one or more analyzer instruments (10) is a digital analyzer designed for collecting digital data and using the digital data for obtaining an analytical testing result.

Proposal 8. The diagnostic analyzing system of any of the preceding Proposals, wherein a distribution characteristic of a data set is determined using a value of the analytical testing result included in the data set.

Proposal 9. The diagnostic analyzing system of any of the preceding Proposals, wherein a distribution characteristic of a data set is determined using metadata associated with the analytical testing result included in the data set.

Proposal 10. The diagnostic analyzing system of any of the preceding Proposals, wherein the metadata at least comprises an age of a patient associated with the analytical testing result.

Proposal 11. The diagnostic analyzing system of any of the preceding Proposals, wherein the metadata at least comprises a gender of a patient associated with the analytical testing result.

Proposal 12. The diagnostic analyzing system of any of the preceding Proposals, wherein the metadata at least comprises a type of sourcing of a patient associated with the analytical testing result.

Proposal 13. The diagnostic analyzing system of any of the preceding Proposals, wherein the metadata at least comprises a ward of a patient associated with the analytical testing result.

Proposal 14. The diagnostic analyzing system of any of the preceding Proposals, wherein the metadata at least comprises a health diagnosis of a patient associated with the analytical testing result.

Proposal 15. The diagnostic analyzing system of any of the preceding Proposals, wherein the monitoring system (20) is designed for:

determining a first characteristic value based on metadata associated with the live data set;

determining a second characteristic value based on metadata associated with the first training data set; and evaluating the difference level using the first characteristic value and the second characteristic value.

Proposal 16. The diagnostic analyzing system of Proposal 15, wherein the first characteristic value and the second characteristic value are each determined using a same characterization algorithm.

Proposal 17. The diagnostic analyzing system of Proposal 16, wherein the characterization algorithm uses the same one or more aspects of metadata of each analytical testing data.

Proposal 18. The diagnostic analyzing system of Proposal 17, wherein the same one or more aspect are at least one of:

an age of a patient associated with the analytical testing result;

a gender of the patient;

a type of sourcing of the patient;

a ward of the patient; and a health diagnosis of the patient.

Proposal 19. The diagnostic analyzing system of any of the preceding Proposals, wherein the monitoring system (20) is designed for:

determining a first association between a first feature of the live data set and a first set of ground-truth labels associated with the live data set, the first set of ground-truth labels being indicative of a validity value of each of the plurality of analytical testing data included in the live data set;

determining a second association between a second feature of the first training data set and a second set of ground-truth labels associated with the first training data set, the second set of ground-truth labels being indicative of a validity value of each of the plurality of training analytical testing data included in the first training data set; and evaluating the difference level using the first association and the second association.

Proposal 20. The diagnostic analyzing system of Proposal 19, wherein the first feature and the second feature comprise at least one of: a value of an analytical testing result and same one or more aspects of metadata of each analytical testing data.

Proposal 21. The diagnostic analyzing system of any of the preceding Proposals, wherein the monitoring system (20) is designed for:

determining a first percentage of analytical testing results of the live data set that are labeled as invalid;

determining a second percentage of analytical testing results of the first training data set that are labeled as invalid;

evaluating the difference level using the first percentage and the second percentage.

Proposal 22. The diagnostic analyzing system of any of the preceding Proposals, wherein the monitoring system (20) is designed for:

obtaining a first performance associated with the original validation algorithm;

determining a second performance associated with the re-trained validation algorithm by processing a testing data set with the re-trained validation algorithm, wherein the testing data set comprises a plurality of analytical testing data; and if the second performance is better than the first performance, using the re-trained validation algorithm for validation of an analytical testing result.

Proposal 23. The diagnostic analyzing system of Proposal 22, wherein the obtaining a first performance associated with the original validation algorithm comprises:

determining the first performance by processing the testing data set using the original validation algorithm.

Proposal 24. The diagnostic analyzing system of any of Proposals 22-23, wherein the training data set are processed by the re-trained validation algorithm according to an order, and wherein the monitoring system (20) is designed for:

determining a first number, the first number being the number of analytical testing results that have been processed by the re-trained validation algorithm before a faulty invalidation is made by the re-trained validation algorithm according to the order;

determining a second number, the second number being the number of analytical testing results before an analytical testing result that is labeled as invalid is processed according to the order; and determining the second performance using the first number of analytical testing data and the second number of analytical testing data.

Proposal 25. The diagnostic analyzing system of any of Proposals 22-24, wherein the monitoring system (20) is designed for:

determining a number of faulty validation predictions and/or faulty invalidation predictions by the re-trained validation algorithm based on the testing data set; and determining the second performance using the number of faulty validation predictions and/or faulty invalidation predictions by the re-trained validation algorithm.

Proposal 26. The diagnostic analyzing system of any of the preceding Proposals, wherein the validation algorithm comprises a first algorithm and a second algorithm, and wherein the first algorithm and the second algorithm are trained such that the first algorithm is stricter than the second algorithm with respect to validating analytical testing data.

Proposal 27. The diagnostic analyzing system of Proposal 26, wherein the second algorithm processes the analytical testing data when the analytical testing result is deemed invalid by the first algorithm.

Proposal 28. The diagnostic analyzing system of any of Proposals 26-27, wherein the monitoring system (20) is designed for generating a first level of warning when the analytical testing data is deemed invalid by the first algorithm, and wherein the monitoring system (20) is designed for generating a second level of warning when the analytical testing data is invalid is deemed invalid by the second algorithm.

Proposal 29. The diagnostic analyzing system of Proposal 28, wherein the second level of warning indicates a higher seriousness than the first level of warning.

Proposal 30. The diagnostic analyzing system of any of the preceding Proposals, wherein the validation algorithm is implemented using a neural network.

Proposal 31. A computer-implemented method for monitoring, e.g. for quality control monitoring, of diagnostic analytical testing, comprising receiving (202) a live data set comprising a plurality of analytical testing data, each analytical testing data comprising an analytical testing result and metadata associated with the analytical testing result;

validating (204) an analytical testing result of the live data set using a validation algorithm;

the validation algorithm being trained using a first training data set comprising a plurality of training analytical testing data, each training analytical testing data comprising a training analytical testing result and training metadata; and evaluating (206) a difference level between the live data set and the first training data set, the difference level being determined based on comparison of distribution characteristics of the live data set and first training data set; and re-training (210) the validation algorithm using a second training set if the difference level between the live data set and the first training data set is greater than a first threshold.

Proposal 32. The computer-implemented method of Proposal 31, further comprising:

using (212) the re-trained validation algorithm for future validation of an analytical testing result.

Proposal 33. The computer-implemented method of any of Proposals 31-32, wherein a difference level between the live data set and the second training data set is lower than a second threshold.

Proposal 34. The computer-implemented method of any of Proposals 31-33, wherein the second training data set comprises the live data set.

Proposal 35. The computer-implemented method of any of Proposals 31-34, further comprising:

performing an analysis of the analytical testing results and the results of the validation algorithm.

Proposal 36. The computer-implemented method of Proposal 35, wherein the method further comprises:

informing a user of a possible error associated with the analyzing testing process based on the analysis.

Proposal 37. The computer-implemented method of any of Proposals 31-36, wherein at least one of the one or more analyzer instruments (10) is a biological sample analyzer designed for processing biological samples and providing an analytical testing result associated with the biological sample.

Proposal 38. The computer-implemented method of any of Proposals 31-37, wherein at least one of the one or more analyzer instruments (10) is a digital analyzer designed for collecting digital data and using the digital data for obtaining an analytical testing result.

Proposal 39. The computer-implemented method of any of Proposals 31-38, wherein a distribution characteristic of a data set is determined using a value of the analytical testing result included in the data set.

Proposal 40. The computer-implemented method of any of Proposals 31-39, wherein a distribution characteristic of a data set is determined using metadata associated with the analytical testing result included in the data set.

Proposal 41. The computer-implemented method of any of Proposals 31-40, wherein the metadata at least comprises an age of a patient associated with the analytical testing result.

Proposal 42. The computer-implemented method of any of Proposals 31-41, wherein the metadata at least comprises a gender of a patient associated with the analytical testing result.

Proposal 43. The computer-implemented method of any of Proposals 31-42, wherein the metadata at least comprises a type of sourcing of a patient associated with the analytical testing result.

Proposal 44. The computer-implemented method of any of Proposals 31-43, wherein the metadata at least comprises a ward of a patient associated with the analytical testing result.

Proposal 45. The computer-implemented method of any of Proposals 31-44, wherein the metadata at least comprises a health diagnosis of a patient associated with the analytical testing result.

Proposal 46. The computer-implemented method of any of Proposals 31-45, wherein the evaluating (206) a difference level between the live data set and the first training data set comprises:

determining a first characteristic value based on metadata associated with the live data set;

determining a second characteristic value based on metadata associated with the first training data set; and evaluating the difference level using the first characteristic value and the second characteristic value.

Proposal 47. The computer-implemented method of Proposal 46, wherein the first characteristic value and the second characteristic value are each determined using a same characterization algorithm.

Proposal 48. The computer-implemented method of Proposal 47, wherein the characterization algorithm uses the same one or more aspects of metadata of each analytical testing data.

Proposal 49. The computer-implemented method of Proposal 48, wherein the same one or more aspects are at least one of:

an age of a patient associated with the analytical testing result;

a gender of the patient;

a type of sourcing of the patient;

a ward of the patient; and a health diagnosis of the patient.

Proposal 50. The computer-implemented method of any of Proposals 31-49, wherein the evaluating (206) a difference level between the live data set and the first training data set comprises:

determining a first association between a first feature of the live data set and a first set of ground-truth labels associated with the live data set, the first set of ground-truth labels being indicative of a validity value of each of the plurality of analytical testing data included in the live data set;

determining a second association between a second feature of the first training data set and a second set of ground-truth labels associated with the first training data set, the second set of ground-truth labels being indicative of a validity value of each of the plurality of training analytical testing data included in the first training data set; and evaluating the difference level using the first association and the second association.

Proposal 51. The computer-implemented method of Proposal 50, wherein the first feature and the second feature comprise at least one of: a value of an analytical testing result and same one or more aspects of metadata of each analytical testing data.

Proposal 52. The computer-implemented method of any of Proposals 50-51, wherein the evaluating (206) a difference level between the live data set and the first training data set comprises:

determining a first percentage of analytical testing results of the live data set that are labeled as invalid;

determining a second percentage of analytical testing results of the first training data set that are labeled as invalid;

evaluating the difference level using the first percentage and the second percentage.

Proposal 53. The computer-implemented method of any of Proposals 31 to 52, wherein the step of re-training of the validation algorithm is only conducted if an additional condition is met.

Proposal 54. The computer-implemented method of any of Proposal 53, wherein the re-trained validation algorithm is used for future validation of an analytical testing result only if a performance condition is met.

Proposal 55. The computer-implemented method of Proposal 54, wherein the using (212) the re-trained validation algorithm for future validation of an analytical testing result comprises:

obtaining a first performance associated with the original validation algorithm;

determining a second performance associated with the re-trained validation algorithm by processing a testing data set with the re-trained validation algorithm, wherein the testing data set comprises a plurality of analytical testing data; and if the second performance is better than the first performance, using the re-trained validation algorithm for validation of an analytical testing result.

Proposal 56. The computer-implemented method of Proposal 55, wherein the obtaining a first performance associated with the original validation algorithm comprises:

determining the first performance by processing the testing data set using the original validation algorithm.

Proposal 57. The computer-implemented method of any of Proposals 55-56, wherein the training data set are processed by the re-trained validation algorithm according to an order, and wherein the determining a second performance associated with the re-trained validation algorithm comprises:

determining a first number, the first number being the number of analytical testing results that have been processed by the re-trained validation algorithm before a faulty invalidation is made by the re-trained validation algorithm according to the order;

determining a second number, the second number being the number of analytical testing results before an analytical testing result that is labeled as invalid is processed according to the order; and determining the second performance using the first number of analytical testing data and the second number of analytical testing data.

Proposal 58. The computer-implemented method of any of Proposals 55-57, wherein the determining a second performance associated with the re-trained validation algorithm comprises:

determining a number of faulty validation predictions and/or faulty invalidation predictions by the re-trained validation algorithm based on the testing data set; and determining the second performance using the number of faulty validation predictions and/or faulty invalidation predictions by the re-trained validation algorithm.

Proposal 59. The computer-implemented method of any of Proposals 31-58, wherein the validation algorithm comprises a first algorithm and a second algorithm, and wherein the first algorithm and the second algorithm are trained such that the first algorithm is stricter than the second algorithm with respect to validating analytical testing data.

Proposal 60. The computer-implemented method of Proposal 58, wherein the second algorithm processes the analytical testing data when the analytical testing result is deemed invalid by the first algorithm.

Proposal 61. The computer-implemented method of any of Proposals 59-60, further comprising:

generating a first level of warning when the analytical testing data is deemed invalid by the first algorithm, and generating a second level of warning when the analytical testing data is invalid is deemed invalid by the second algorithm.

Proposal 62. The computer-implemented method of Proposal 61, wherein the second level of warning indicates a higher seriousness than the first level of warning.

Proposal 63. The computer-implemented method of any of Proposals 31-62, wherein the validation algorithm is implemented using a neural network.

Proposal 64. A method for monitoring of diagnostic analytical testing, comprising:

determining a plurality of analytical testing results;

providing a live data set comprising a plurality of analytical testing data, each analytical testing data comprising an analytical testing result of the plurality of analytical testing results and metadata associated with the analytical testing result; and performing the steps of the computer-implemented method according to any of Proposals 31-63.

Proposal 65. A diagnostic analyzing system (1), comprising one or more analyzer instruments (10) designed for determining analytical testing results;

a monitoring system (20) being configured for performing the computer-implemented method according to one of Proposals 31-63.

Proposal 66. The diagnostic analyzing system of Proposal 65, wherein at least one of the one or more analyzer instruments (10) is a biological sample analyzer (10) designed for processing biological samples and providing an analytical testing result associated with the biological sample.

Proposal 67. The diagnostic analyzing system of any of Proposals 65-66, wherein at least one of the one or more analyzer instruments (10) is a digital analyzer designed for collecting digital data and use the digital data for obtaining an analytical testing result.

Proposal 68. A monitoring system (20) for diagnostic analytical testing, wherein the monitoring system (20) is designed for:

processing an analytical testing data, the analytical testing data comprising an analytical testing result provided by one or more analyzer instruments (10) and metadata associated with the analytical testing result, validating an analytical testing result using a validation algorithm, the validation algorithm being trained using a first training data set comprising a plurality of training analytical testing data, each training analytical testing data comprising a training analytical testing result and training metadata, and evaluating a difference level between a live data set of analytical testing data and the first training data set, the difference level being determined based on a comparison of distribution characteristics of the live data set and the first training data set, and re-training the validation algorithm using a second training data set if the difference level between the live data set and the first training data set is greater than a first threshold, and using the re-trained validation algorithm for validation of an analytical testing result.

This proposal 68 can be implemented according to the features of the Proposals 2 to 30.

Proposal 69. A computer-implemented method for monitoring of diagnostic related analytical testing, comprising processing an analytical testing data, the analytical testing data comprising an analytical testing result provided by one or more analyzer instruments (10) and metadata associated with the analytical testing result, validating an analytical testing result using a validation algorithm, the validation algorithm being trained using a first training data set comprising a plurality of training analytical testing data, each training analytical testing data comprising a training analytical testing result and training metadata, and evaluating a difference level between a plurality of analytical testing data being processed and the first training data set, the difference level being determined based on a comparison of distribution characteristics of the plurality of analytical testing data being processed and the first training data set.

Proposal 70. The computer implemented method of Proposal 69, further comprising:

re-training the validation algorithm using a second training data set if the difference level between the plurality of analytical testing data being processed and the first training data set is greater than a first threshold, and using the re-trained validation algorithm for future validation of an analytical testing result.

These Proposals 69 and 70 can each be implemented according to the features of the proposals 31 to 63, wherein the "plurality of analytical testing data being processed" plays the role of the "live data set".

Proposal 71. A monitoring system (20) for diagnostic analytical testing, comprising:

a processing unit (701); and a memory (702, 703) coupled to the processing unit and having instructions stored thereon that, when executed by the processing unit, cause the electronic device to perform the method according to any of Proposals 31-63.

Proposal 72. A computer-readable medium comprising instructions that when executed cause performing the method according to any of Proposals 31 to 63.

Further proposed are systems that are designed for performing the proposed methods and/or parts thereof. The proposed methods can, at least partially, be realized as computer-implemented methods.

Further proposed are computer-readable mediums comprising instructions that, when executed, cause performing the proposed methods and/or parts thereof.

Further proposed are methods embodied by the proposed systems.

We claim:

1. A diagnostic analyzing system, comprising:

one or more analyzer instruments configured to determine an analytical testing result, associated with a physical in vitro biological sample, by processing the physical in vitro biological sample using at least one of chemical, biological, physical, or optical procedures; and a monitoring system configured to:

obtain analytical testing data comprising:

the analytical testing result determined by the one or more analyzer instruments; and metadata associated with the analytical testing result;

generate, using a validation machine learning algorithm, a validation determination indicating whether the analytical testing result, determined by the one or more analyzer instruments, is valid or invalid, wherein:

the validation machine learning algorithm is trained based on a first training data set comprising:

at least one training analytical testing result, and training metadata;

determine a difference level between a live data set and the first training data set, wherein:

the live data set comprises the analytical testing data, and the difference level is determined based on a comparison of distribution characteristics of the live data set and the first training data set;

determine that the difference level is greater than a threshold;

re-train, in response to determining that the difference level is greater than the threshold, the validation machine learning algorithm based on a second training data set having characteristics corresponding with the distribution characteristics of the live data set; and use the re-trained validation machine learning algorithm for validation of at least one of the analytical testing result or a second analytical testing result.

2. The diagnostic analyzing system of claim 1, wherein a second difference level between the live data set and the second training data set is lower than a second threshold.

3. The diagnostic analyzing system of claim 1, wherein the second training data set comprises the live data set.

4. The diagnostic analyzing system of claim 1, wherein the monitoring system is configured to present output indicative of a possible error associated with an analyzing testing process based on the validation determination indicating that the analytical testing result is invalid.

5. The diagnostic analyzing system of claim 1, wherein the distribution characteristics are determined based on the at least one training analytical testing result indicated by the first training data set and the analytical testing result indicated by the live data set.

6. The diagnostic analyzing system of claim 1, wherein the distribution characteristics are determined based on the training metadata indicated by the first training data set and the metadata associated with the analytical testing result indicated by the live data set.

7. The diagnostic analyzing system of claim 1, wherein the metadata indicates at least one of:
an age of a patient associated with the analytical testing result,
a gender of the patient,
a type of sourcing of the patient,
a ward of the patient, or
a health diagnosis of the patient.

8. The diagnostic analyzing system of claim 1, wherein the monitoring system is programmed and configured to:
determine a first characteristic value based on the metadata associated with the live data set;
determine a second characteristic value based on the training metadata associated with the first training data set; and
determine the difference level using the first characteristic value and the second characteristic value.

9. The diagnostic analyzing system of claim 1, wherein the monitoring system is programmed and configured to:
determine a first association between a first feature of the live data set and a first set of ground-truth labels associated with the live data set, the first set of ground-truth labels being indicative of first validity values respectively corresponding to analytical testing data instances included in the live data set;
determine a second association between a second feature of the first training data set and a second set of ground-truth labels associated with the first training data set, the second set of ground-truth labels being indicative of second validity values respectively corresponding to training analytical testing data instances included in the first training data set; and
determine the difference level using the first association and the second association.

10. The diagnostic analyzing system of claim 1, wherein the monitoring system is programmed and configured to:
determine a first percentage of analytical testing results of the live data set that are labeled as invalid;
determine a second percentage of training analytical testing results of the first training data set that are labeled as invalid; and
determine the difference level using the first percentage and the second percentage.

11. The diagnostic analyzing system of claim 1, wherein the monitoring system is programmed and configured to:
determine a first performance associated with a first version of the validation machine learning algorithm;
determine a second performance associated with the re-trained validation machine learning algorithm by processing a testing data set with the re-trained validation machine learning algorithm, wherein the testing data set comprises a plurality of analytical testing data; and
in response to determining that the second performance is better than the first performance, using the re-trained validation machine learning algorithm for validation of the at least one of the analytical testing result or the second analytical testing result.

12. The diagnostic analyzing system of claim 11, wherein the testing data set is processed by the re-trained validation machine learning algorithm according to an order, and wherein the monitoring system is programmed and configured to:
determine a first number of analytical testing results that have been processed by the re-trained validation machine learning algorithm before a faulty invalidation is made by the re-trained validation machine learning algorithm according to the order;
determine a second number of the analytical testing results before one of the analytical testing results that is labeled as invalid is processed according to the order; and
determine the second performance using the first number and the second number.

13. The diagnostic analyzing system of claim 11, wherein the monitoring system is programmed and configured to:
determine a number of at least one of faulty validation predictions or faulty invalidation predictions, by the re-trained validation machine learning algorithm, based on the testing data set; and
determine the second performance using the number of the at least one of the faulty validation predictions or the faulty invalidation predictions by the re-trained validation machine learning algorithm.

14. The diagnostic analyzing system of claim 1, wherein the monitoring system is configured to:
validate the analytical testing result using a first version of the validation machine learning algorithm and the re-trained validation machine learning algorithm,
associate the analytical testing result with a first level of warning based on the analytical testing result being determined to be invalid by the first version of the validation machine learning algorithm and being determined to be valid by the re-trained validation machine learning algorithm, and
associate the analytical testing result with a second level of warning based on the analytical testing result being determined to be invalid by both the first version of the validation machine learning algorithm and the re-trained validation machine learning algorithm.

15. The diagnostic analyzing system of claim 1, wherein the one or more analyzer instruments comprise at least one of a laboratory biological sample analyzer system or a point-of-care system.

16. A computer-implemented method for quality control monitoring of diagnostic analytical testing, comprising:
receiving a live data set comprising analytical testing data associated with testing of one or more physical in vitro biological samples by one or more analyzer instruments, wherein the analytical testing data indicates:
an analytical testing result determined by the one or more analyzer instruments based on processing of the one or more physical in vitro biological samples, and
metadata associated with the analytical testing result;
generating, using a validation machine learning algorithm, a validation determination indicating whether the analytical testing result, determined by the one or more analyzer instruments, is valid or invalid, wherein:
the validation machine learning algorithm is trained based on a first training data set comprising:
at least one training analytical testing result, and
training metadata;
determining a difference level between the live data set and the first training data set, based on comparison of distribution characteristics of the live data set and the first training data set;
determining that the difference level is greater than a threshold; and re-training, in response to determining that the difference level is greater than the threshold, the validation machine learning algorithm based on a second training data set having characteristics corresponding with the distribution characteristics of the live data set.

17. A method for monitoring of diagnostic analytical testing, comprising:

determining, by testing physical in vitro biological samples with one or more analyzer instruments using at least one of chemical, biological, physical, or optical procedures, a plurality of analytical testing results associated with the testing of the physical in vitro biological samples;

providing a live data set comprising:

the plurality of analytical testing results, and metadata associated with the plurality of analytical testing results;

generating, using a validation machine learning algorithm, a validation determination indicating whether at least one analytical testing result, determined by the one or more analyzer instruments, is valid or invalid, wherein:

the validation machine learning algorithm is trained based on a first training data set comprising:

at least one training analytical testing result, and training metadata;

determining a difference level between the live data set and the first training data set, based on comparison of distribution characteristics of the live data set and the first training data set;

determining that the difference level is greater than a threshold;

re-training, in response to determining that the difference level is greater than the threshold, the validation machine learning algorithm based on a second training data set having characteristics corresponding with the distribution characteristics of the live data set; and using the re-trained validation machine learning algorithm for validation of a second analytical testing result indicated by at least one of the live data set or a second live data set.

18. A diagnostic analyzing system, comprising:

one or more analyzer instruments programmed and configured to determine analytical testing results associated with testing of one or more physical in vitro biological samples; and a monitoring system being configured to:

receive a live data set comprising:

the analytical testing results determined by the one or more analyzer instruments, and metadata associated with the analytical testing results;

generate, using a validation machine learning algorithm, a validation determination indicating whether at least one of the analytical testing results, determined by the one or more analyzer instruments, is valid or invalid, wherein:

the validation machine learning algorithm is trained based on a first training data set comprising:

a training analytical testing result, and training metadata;

determine a difference level between the live data set and the first training data set, based on comparison of distribution characteristics of the live data set and the first training data set;

determine that the difference level is greater than a threshold; and re-train the validation machine learning algorithm, in response to determining that the difference level is greater than the threshold, based on a second training data set having characteristics corresponding with the distribution characteristics of the live data set.

19. A monitoring system for diagnostic analytical testing, wherein the monitoring system is programmed and configured to:

process analytical testing data comprising:

an analytical testing result determined by one or more analyzer instruments via processing of one or more physical in vitro biological samples, and metadata associated with the analytical testing result;

generate, using a validation machine learning algorithm, a validation determination indicating whether the analytical testing result, determined by the one or more analyzer instruments, is valid or invalid, wherein:

the validation machine learning algorithm is trained based on a first training data set comprising:

a training analytical testing result, and training metadata;

determine a difference level between a live data set and the first training data set, based on a comparison of distribution characteristics of the live data set and the first training data set, wherein the live data set comprises the analytical testing data;

determine that the difference level is greater than a threshold;

re-train, in response to determining that the difference level is greater than the threshold, the validation machine learning algorithm based on a second training data set having characteristics corresponding with the distribution characteristics of the live data set; and validate at least one of the analytical testing result or a second analytical testing result using the re-trained validation machine learning algorithm.

20. A computer-implemented method for monitoring of diagnostic related analytical testing, comprising:

determining analytical testing data, associated with testing of one or more physical in vitro biological samples by one or more analyzer instruments, comprising:

an analytical testing result determined by the one or more analyzer instruments by processing the one or more physical in vitro biological samples using at least one of chemical, biological, physical, or optical procedures, and metadata associated with the analytical testing result;

generating, using a validation machine learning algorithm, a validation determination indicating whether the analytical testing result is valid or invalid, wherein:

the validation machine learning algorithm is trained based on a first training data set comprising:

a training analytical testing result, and training metadata;

determining a difference level between the analytical testing data and the first training data set, based on a comparison of distribution characteristics of the analytical testing data and the first training data set;

determining that the difference level is greater than a threshold; and re-training, in response to determining that the difference level is greater than the threshold, the validation machine learning algorithm based on a second training data set having characteristics corresponding with the distribution characteristics of the analytical testing data.

21. A monitoring system for diagnostic analytical testing, comprising:

a processing unit; and a memory coupled to the processing unit and having instructions stored thereon that, when executed by the processing unit, cause the monitoring system to:

receive a live data set associated with testing of one or more in vitro biological samples by one or more analyzer instruments, the live data set comprising analytical testing data indicating:

an analytical testing result determined by the one or more analyzer instruments, and metadata associated with the analytical testing result;

generate, using a validation machine learning algorithm, a validation determination indicating whether the analytical testing result is valid or invalid, wherein:

the validation machine learning algorithm is trained based on a first training data set that comprises:

a training analytical testing result, and training metadata;

determine a difference level between the live data set and the first training data set, based on a comparison of distribution characteristics of the live data set and the first training data set;

determine that the difference level is greater than a threshold; and re-train, in response to determining that the difference level is greater than the threshold, the validation machine learning algorithm based on a second training data set having characteristics corresponding with the distribution characteristics of the live data set.

22. A non-transitory computer-readable medium comprising instructions that, when executed by one or more processors of a monitoring system, cause the monitoring system to:

receive a live data set associated with testing of one or more in vitro biological samples by one or more analyzer instruments, the live data set comprising analytical testing data indicating:

an analytical testing result determined by the one or more analyzer instruments, and metadata associated with the analytical testing result;

generate, using a validation machine learning algorithm, a validation determination indicating whether the analytical testing result is valid or invalid, wherein:

the validation machine learning algorithm is trained based on a first training data set that comprises:

a training analytical testing result, and training metadata;

determine a difference level between the live data set and the first training data set, based on a comparison of distribution characteristics of the live data set and the first training data set;

determine that the difference level is greater than a threshold; and re-train, in response to determining that the difference level is greater than the threshold, the validation machine learning algorithm based on a second training data set having characteristics corresponding with the distribution characteristics of the live data set.

* * * * *